(12) United States Patent
Yang et al.

(10) Patent No.: US 10,330,463 B2
(45) Date of Patent: Jun. 25, 2019

(54) SPATIAL PHASE-SHIFT SHEAROGRAPHY SYSTEM FOR NON-DESTRUCTIVE TESTING AND STRAIN MEASUREMENT

(71) Applicant: OAKLAND UNIVERSITY, Rochester, MI (US)

(72) Inventors: Lianxiang Yang, Rochester Hills, MI (US); Xin Xie, Auburn Hills, MI (US); Nan Xu, Auburn Hills, MI (US); Xu Chen, Auburn Hills, MI (US)

(73) Assignee: Oakland University, Rochester, MI (US)

( * ) Notice: Subject to any disclaimer, the term of this patent is extended or adjusted under 35 U.S.C. 154(b) by 0 days.

(21) Appl. No.: 15/032,577

(22) PCT Filed: Oct. 28, 2014

(86) PCT No.: PCT/US2014/062610
§ 371 (c)(1),
(2) Date: Apr. 27, 2016

(87) PCT Pub. No.: WO2015/065999
PCT Pub. Date: May 7, 2015

(65) Prior Publication Data
US 2016/0265900 A1 Sep. 15, 2016

Related U.S. Application Data

(60) Provisional application No. 61/896,391, filed on Oct. 28, 2013.

(51) Int. Cl.
*G01B 9/02* (2006.01)
*G01L 1/24* (2006.01)
(Continued)

(52) U.S. Cl.
CPC ........ *G01B 9/02098* (2013.01); *G01B 11/162* (2013.01); *G01L 1/24* (2013.01); *G01N 21/45* (2013.01); *G01N 21/8806* (2013.01)

(58) Field of Classification Search
CPC .................................................. G01B 11/162
See application file for complete search history.

(56) References Cited

U.S. PATENT DOCUMENTS 6,433,874 B2   8/2002  Lindsay et al.
2003/0103212 A1  6/2003  Westphal et al.
(Continued)

FOREIGN PATENT DOCUMENTS

DE  4036120 A1   5/1992
DE  4102881 A1   8/1992
DE  19513233 A1  10/1996

OTHER PUBLICATIONS

Kästle, Ralf, Erwin Hack, and Urs Sennhauser. "Multiwavelength shearography for quantitative measurements of two-dimensional strain distributions." Applied optics 38.1 (1999): 96-100.*
(Continued)

*Primary Examiner* — Kara E. Geisel
*Assistant Examiner* — Rufus L Phillips
(74) *Attorney, Agent, or Firm* — Fishman Stewart PLLC

(57) ABSTRACT

Embodiments of a shearography system may include light sources configured to produce beams of light to illuminate a test area. Each of the beams of light may include a different wavelength. A camera may be configured to obtain intensity information corresponding to reflections of the lights off of the test area. An optical shearing device may be disposed in an optical path between the light sources and the camera and the optical shearing device may be configured to provide a shearing angle.

14 Claims, 14 Drawing Sheets

(51) Int. Cl.
*G01B 11/16* (2006.01)
*G01N 21/45* (2006.01)
*G01N 21/88* (2006.01)

(56) References Cited

U.S. PATENT DOCUMENTS

| | | | | |
|---|---|---|---|---|
| 2010/0309476 | A1* | 12/2010 | Millerd | G01B 11/2441 356/495 |
| 2011/0157599 | A1* | 6/2011 | Weaver | G01D 5/266 356/496 |
| 2012/0038930 | A1* | 2/2012 | Sesko | G01B 11/026 356/486 |
| 2013/0114088 | A1 | 5/2013 | Newman | |

OTHER PUBLICATIONS

Groves, Roger M., Stephen W. James, and Ralph P. Tatam. "Multicomponent shearography employing four measurements channels." Speckle Metrology 2003. International Society for Optics and Photonics, 2003.*

Charrett et al. "Quantitative shearography: error reduction by using more than three measurement channels", Applied optics 50.2 (2011) 134-146.*

Francis, D., S. W. James, and R. P. Tatam. "Surface strain measurement using multi-component shearography with coherent fibre-optic imaging bundles." Measurement Science and Technology 18.11 (2007): 3583.*

Kemao, Qian. "Windowed Fourier transform for fringe pattern analysis." Applied Optics 43.13 (2004): 2695-2702.*

Pedrini, G., Y. L. Zou, and H. J. Tiziani. "Quantitative evaluation of digital shearing interferogram using the spatial carrier method." Pure and Applied Optics: Journal of the European Optical Society Part A 5.3 (1996): 313.*

USPTO, International Search Report and Written Opinion in corresponding international application No. PCT/US2014/062610, dated Jan. 22, 2015.

Xie, X. et al, Michelson interferometer based spatial phase shift shearography. Applied Optics, Vo. 52, No. 17, Jun. 10, 2013, pp. 4063-4071.

Xie, X. et al, Review and Comparison of Temporal and Spatial-Phase Shift Speckle Pattern Interferometry for 3D Deformation Measurement, Sixth Int'l Symposium on Precision Mechanical Measurements, Oct. 10, 2013, SPIE vol. 8916, 89160D.

Yang, L. et al, Fast non-destructive testing under dynamic loading. SPIE Newsroom, Nov. 7, 2013.

Zhu, Lianqing et al, Real-time monitoring of phase maps of digital shearography. Oct. 2013. SPIE vol. 52(10).

European Search Report, EP 14 85 6846, dated May 15, 2017.

* cited by examiner

SPATIAL PHASE-SHIFT SHEAROGRAPHY SYSTEM FOR NON-DESTRUCTIVE TESTING AND STRAIN MEASUREMENT

CROSS REFERENCE TO RELATED APPLICATIONS

This application is a national stage filing based upon International PCT Application No. PCT/US2014/062610, with an international filing date of Oct. 28, 2014, which claims the benefit of priority to U.S. Provisional application No. 61/896,391 filed 28 Oct. 2013, the entire disclosures of which are hereby incorporated by reference as though fully set forth herein.

TECHNICAL FIELD

The present disclosure relates to methods and systems for measuring stress, strain, and/or deformation. Strain measurement is often used in a variety of applications, including manufacturing, biomedical, and microelectronics, among others. For example, aircrafts are often analyzed using shearography.

BACKGROUND

Conventional shearography systems typically have several drawbacks that prevent effective use for analyzing dynamic systems. For example, conventional systems may require acquisition of at least two images before loading and at least two images after loading. Acquisition of multiple images before and after loading may undesirably increase processing time.

Additionally, conventional shearography systems may include complicated structures that prohibit wide commercial adoption, particularly for field applications.

SUMMARY

The present disclosure includes a shearography system that may include a plurality of light sources each configured to produce a beam of light to illuminate a test area, each of the beams of light having a different wavelength. In embodiments, a shearography system may include a camera configured to obtain intensity information corresponding to reflections of the plurality of lights off of the test area. In embodiments, a shearography system may include an optical shearing device disposed in an optical path between the plurality of light sources and the camera, the optical shearing device configured to provide a shearing angle. In embodiments, the camera may be configured to obtain intensity information corresponding to simultaneous reflections of the plurality of lights off of the test area. In embodiments, captured intensity information may allow for the calculation of in-plane normal strain, in-plane shear strain, and/or pure out-of-plane shear strain from a single testing image.

In embodiments, a method of determining strain may include illuminating, via a plurality of light sources, a test area of a test object, capturing, via a camera, a first plurality of interferograms corresponding to the test area, the first plurality of interferograms being captured in a reference image, determining a reference phase difference from the reference image, capturing, via the camera, a second plurality of interferograms corresponding to the test area, the second plurality of interferograms being captured in a testing image, determining a testing phase difference from the testing image, and determining a strain measurement according to a relative phase difference between the reference phase difference and the testing phase difference. In embodiments, each of the light sources of the plurality of light sources may be configured to produce a beam of light, and the beam of light produced by each light source may have a different wavelength than the lights produced by the other light sources.

Various aspects of this invention will become apparent to those skilled in the art from the following detailed description of the preferred embodiment, when read in light of the accompanying drawings.

DETAILED DESCRIPTION

Reference will now be made in detail to embodiments of the present disclosure, examples of which are described herein and illustrated in the accompanying drawings. While the invention will be described in conjunction with embodiments and examples, it will be understood that they are not intended to limit the invention to these embodiments. On the contrary, the invention is intended to cover alternatives, modifications and equivalents, which may be included within the spirit and scope of the invention as defined by appended claims.

The present disclosure includes a shearography system 100. Shearography system 100 may be referred to as a digital speckle pattern shearing interferometry system and may be used for non-destructive testing (NDT) to analyze properties of various materials, such as, for example, composite materials. Shearography system 100 may be configured laser-based, full field, non-contact optical measurement of strain (e.g., in-plane strain) with a sensitivity of several microstrains.

Figure 1A:
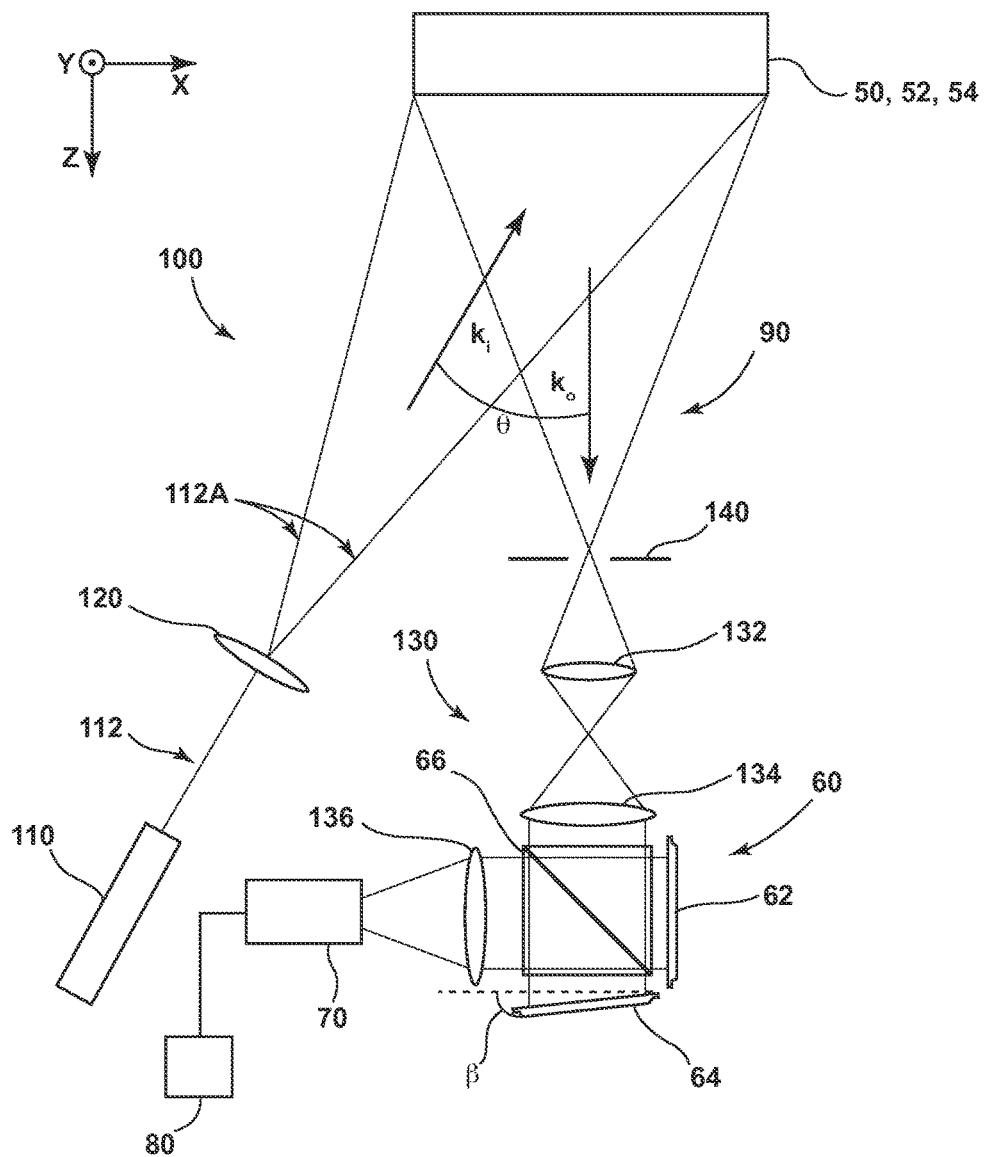
FIG. 1A is a schematic view of an embodiment of a shearography system in accordance with teachings of the present disclosure.

As generally illustrated in FIG. 1A, in embodiments, shearography system 100 may include an optical shearing device 60, a detector 70, a first light source 110, a beam expander 120, a plurality of lenses 130, and/or an aperture 140. In embodiments, first light source 110 configured to illuminate a test object 50. Test object may include a first state 52, which may correspond to a reference, unloaded, and/or non-deformed state. Additionally or alternatively, test object 50 may include a second state 54, which may include a loaded and/or deformed state. In embodiments, second state of test object 50 may include one or more of a variety of loads and/or deformations.

In embodiments, first light source 110 may illuminate test object 50, which may allow detector 70 to capture a reference image (e.g., a reference shearogram). A reference shearogram may correspond to a first beam 112 from first light source 110 illuminating test object 50 and may be captured by detector 70 via optical shearing device 60. First light source 110 may then illuminate test object 50 again, but with test object 50 in second state 54, which may allow for generating a corresponding testing image (e.g., a testing shearogram). Comparing a reference image with a testing image may allow for a determination of relative phase difference information, which may be used to measure stress, strain, and/or deformation, and/or locate faults in a material.

In embodiments, a light source (e.g., first light source 110) may be configured to emit convergent, generally convergent, and/or partially convergent light, such as, for example, first beam 112. In embodiments, a light source may be configured to emit coherent, generally coherent, and/or partially coherent light. In embodiments, a light source may include a laser, first beam 112 may be configured as a laser beam, and/or first beam of light 112 may be referred to herein as first laser beam 112. In embodiments, a light source may include a helium-neon (HeNe) laser, which may be configured to emit a laser beam including a wavelength of about 630 nm, for example, 632.8 nm. For example, and without limitation, first beam of light 112 may be configured as a laser with a wavelength of about 632.8 nm. Additionally or alternatively, a light source may include a green laser, which may be configured to emit a laser beam including a wavelength of about 532 nm. For example, and without limitation, first beam of light 112 may be configured as a laser with a wavelength of about 532 nm. In embodiments, a light source may be configured to illuminate test object 50 and/or may be configured to direct first beam of light 112 toward test object 50.

Shearography system 100 may include one or more beam expanders 120. A beam expander 120 may be configured to expand a beam of light into an expanded beam of light, such as, for example, first beam of light 112 into expanded first beam of light 112A. Beam expander 120 may be disposed in an optical path 90 between a light source (e.g., first light source 110) and testing object 50.

Detector 70 may be configured to detect, receive, capture, and/or measure light and/or the intensity of light. Detector 70 may also be referred to herein as camera 70. In embodiments, camera 70 may include a charge-coupled device (CCD). A CCD may be configured to determine a value of light intensity provided to it. In embodiments, for example only, intensity may be measured on a scale of 0 to 255. In embodiments, a shearography system (e.g., shearography systems 100, 200, 300), may include a single camera 70 or a plurality of cameras.

In embodiments, camera 70 may include a high speed camera, such as, for example, a camera capable of capturing at least 15,000 frames per second (fps). A high speed camera may allow a shearography system to include a dynamic measurement range of up to and/or exceeding 7.5 kHz.

Figure 1B:
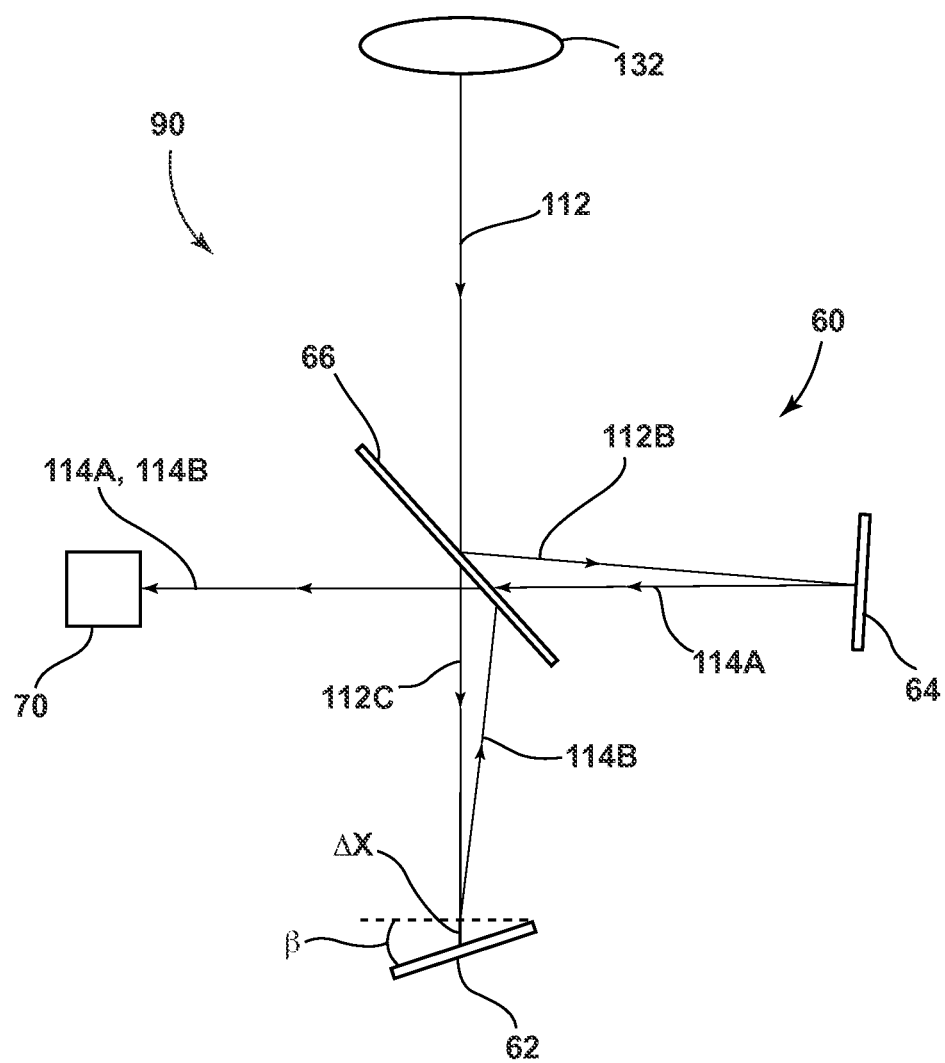
FIG. 1B is a schematic view of portions of an embodiment of a shearography system in accordance with teachings of the present disclosure.

In embodiments, shearography system 100 may include aspects that generally correspond to a Michelson interferometer and/or may include a Michelson-based spatial phase-shift shearography system. For example, optical shearing device 60 may include an interferometer, such as, for example, a modified Michelson interferometer. In embodiments, camera 70 may include portions and/or all of optical shearing device 60. As generally illustrated in FIG. 1B, in embodiments, optical shearing device 60 may include a first element 62, a second element 64, and/or a third element 66. First element 62 may be configured to reflect light, may include mirror 62, and/or may be referred to herein as mirror 62. Second element may configured to reflect light, may include mirror 64, and/or may be referred to herein as mirror 64. Mirror 62 and mirror 64 may be disposed in generally perpendicular orientation relative to one another. In embodiments, optical shearing device may be configured to provide a shearing angle β, which may include at least one of mirrors 62, 64 may be disposed such that it is not perpendicular relative to the other mirror. For example, mirror 64 may be disposed at an angle β relative to mirror 62, and angle β may comprise an oblique angle. In embodiments, optical shearing device may be disposed in an optical path (e.g., optical path 90) between a light source (e.g., first light source 110, second light source 210, etc.) and camera 70.

In embodiments, a mirror (e.g., mirror 64) disposed at angle β may be configured to introduce a frequency component to a beam of light and/or angle may be referred to as shearing angle β. For example, and without limitation, mirror 64 disposed at angle β may be configured to introduce a frequency component to first beam of light 112. A frequency component introduced into a beam of light may correspond to a wavelength of the beam of light. For example, and without limitation, frequency component $f_1$ may correspond to a wavelength of first beam of light. Frequency components may be introduced in such a way that after a Fourier transform, phase information may be extracted or derived from a resulting spectrum. Extracting phase information may be accomplished via a windowed inverse Fourier transform (WIFT) and/or via a filter, such as a band pass filter, a gate function filter, and/or a normal function filter. In embodiments, for example, phase information may include a range from 0 to $2\pi$.

In embodiments, third element 66 may include a beam splitter and/or may be referred to herein as beam splitter 66. Beam splitter 66 may include one or more of a variety of configurations. For example, and without limitation, beam splitter 66 may include a cube, which may include two triangular prisms joined together, and/or beam splitter may include a half-silvered element. Beam splitter 66 may be configured such that all of, a portion of, or none of the light that is directed to beam splitter 66 passes through beam splitter 66. In embodiments, beam splitter 66 may be configured to reflect light that does not pass through it. In embodiments, beam splitter 66 may be configured to reflect a first portion of first beam 112B toward mirror 62. Additionally or alternatively, beam splitter 66 may be configured to receive first beam 112 and allow a second portion 112C of first beam 112 to pass through to mirror 64. In embodiments, beam splitter 66 may be configured to allow first portion 112B of first beam 112, which may include about half of first beam 112, to pass through to mirror 64, and/or beam splitter 66 may be configured to reflect second portion 112C, which may include about half of first beam 112, toward mirror 62. Beam splitter 66 may, additionally or alternatively, be configured to allow light reflected from mirror 62 (e.g., first beam second portion 112C) to pass through toward camera 70 as a first wave front 114A and/or reflect light reflected from mirror 64 (e.g., second portion 112C) toward camera 70 as a second wave front 114B.

In embodiments, camera 70 may be configured to capture first wave front 114A corresponding to first portion 112B of first beam 112 and/or capture second wave front 114B corresponding to second portion 112C of first beam 112. The first and second wave fronts 114A, 114B may be represented via the following equations, respectively:

$$u_1(x,y)=|u_1(x,y)|\exp[i\varphi(x,y)] \qquad \text{Eq. 1.}$$

$$u_2(x,y)=|u_2(x+\Delta x,y)|\exp\{i\varphi(x+\Delta x,y)+2\pi i f_0 x\} \qquad \text{Eq. 2.}$$

where $u_1$ corresponds to first wave front 114A, $u_2$ corresponds to second wave front 114B, and $\Delta x$ corresponds to the shearing distance in the x direction, which may correspond to shearing angle $\beta$.

The $f_0$ value may represent the spatial frequency component introduced by second mirror 64 being disposed at shearing angle $\beta$. The $f_0$ value may be represented by the following equation:

$$f_0 = (\sin \beta/\lambda) \qquad \text{Eq. 3.}$$

where $\lambda$ corresponds to a wavelength of first light source 110.

An intensity of light provided to and/or captured by camera 70 may be represented by:

$$I=(u_1+u_2)(u_1{}^*+u_2{}^*)=u_1 u_1{}^*+u_2 u_2{}^*+u_1 u_2{}^*+u_2 u_1{}^* \qquad \text{Eq. 4.}$$

where * corresponds to a complex conjugate of $u_i$ (e.g., $u_1{}^*$ may correspond to a complex conjugate of $u_1$).

A Fourier transform of the speckle interferogram (e.g., of the intensity equation, Eq. 4), may convert the captured image into the frequency (Fourier) domain from the spatial domain. A Fourier transform of Eq. 4 may be represented by:

$$FT(I) = \qquad \text{Eq. 5}$$
$$U_1(f_x, f_y) \otimes U_1 *(f_x, f_y) + U_2(f_x+f_0, f_y) \otimes U_2 *(f_x+f_0, f_y) +$$
$$U_1(f_x, f_y) \otimes U_2 *(f_x+f_0, f_y) + U_2(f_x+f_0, f_y) \otimes U_1 *(f_x, f_y).$$

where $\otimes$ corresponds to a convolution operation, $U_1(f_x, f_y)$ corresponds to a Fourier transform of first wave front 114A ($u_1$), and $U_2(f_x+f_0, f_y)$ corresponds to a Fourier transform of second wave front 114B ($u_2$).

Figure 2A:
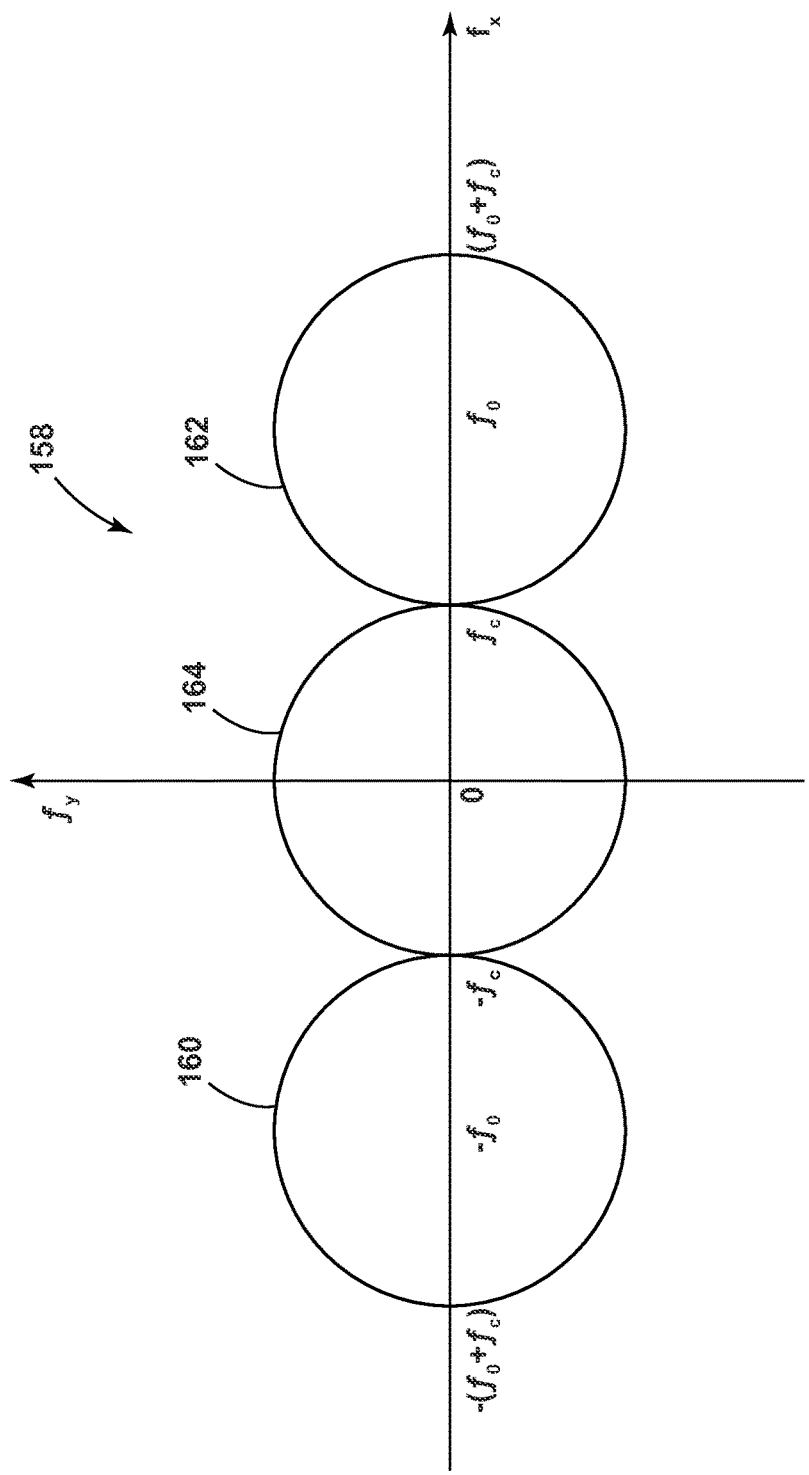
FIGS. 2A and 2B are spectrums corresponding to an embodiment of a shearography system in accordance with teachings of the present disclosure.

In embodiments, an ideal version 158 of spectrum 150 that may result from a Fourier transform corresponding to Equation 5 is generally illustrated in FIG. 2A. An ideal spectrum 158 may include a first portion 160 that may be located at or about $(-f_0, 0)$ and may correspond to the $U_1 \otimes U_2{}^*$ term. Second portion 162 of spectrum 158 may be generally located at or about $(f_0, 0)$ and may generally correspond to the $U_2 \otimes U_1{}^*$ term. The remaining two terms, $U_1 \otimes U_1{}^*$ and $U_2 \otimes U_2{}^*$, may include relatively low frequency components and may generally correspond to third portion 164 which may be located at or about (0, 0). As first portion 160 and/or second portion 162 may include useful phase information, it may be desirable if first portion 160 and/or second portion 162 are distinct and/or distinguishable from the third portion 164 (e.g., center) of spectrum 158, which may not include useful information.

Figure 2B:
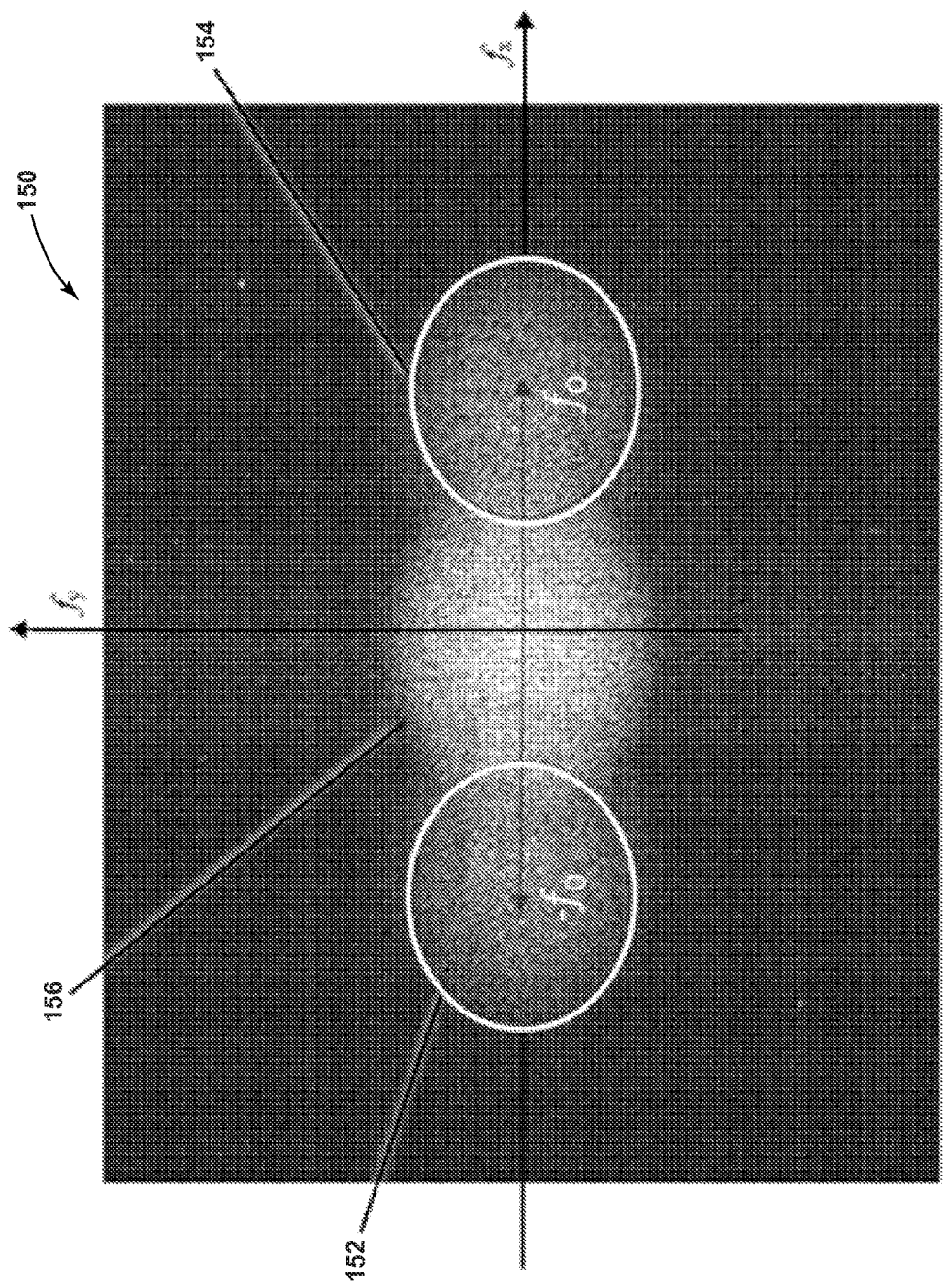

In practice, spectrum 150 may not be as easily distinguishable as ideal spectrum 158 and/or may more closely resemble the spectrum illustrated in FIG. 2B. As generally illustrated in FIG. 2B, spectrum 150 may generally include a first portion 152, a second portion 154, and/or a third portion 156, which may generally correspond to respective terms of Equation 5. For example, first portion 152 of spectrum 150 may be generally located at or about $(-f_0, 0)$ and may correspond to the $U_1 \otimes U_2{}^*$ term. Second portion 154 of spectrum 150 may be generally located at or about $(f_0, 0)$ and may generally correspond to the $U_2 \otimes U_1{}^*$ term. The remaining two terms, $U_1 \otimes U_1{}^*$ and $U_2 \otimes U_2{}^*$, may include relatively low frequency components and may generally correspond to third portion 156, which may be located at or about (0, 0). These two terms may correspond to background light and/or may not include desired information.

In embodiments, first portion 152 and/or second portion 154 of spectrum may contain phase information of the captured interferogram (e.g., reference interferogram and/or testing interferogram). A windowed inverse Fourier transform (WIFT) may be applied to spectrum 150 to extract phase information from first portion 152 and/or second portion 154. In embodiments, a window of the windowed inverse Fourier transform may correspond to (e.g., be centered at) frequency component $f_0$ which may correspond to the wavelength of first beam 112 and the shearing angle (see, e.g., Equation 3) and/or the window may include a width of $2f_{c1}$ (see, e.g., Equation 11, below). Applying a WIFT may result in the following equation:

$$[\Phi + 2\pi x f_0] = \arctan\frac{\text{Im}[u_2 u_1^*]}{\text{Re}[u_2 u_1^*]}. \qquad \text{Eq. 6}$$

where Im may correspond to an imaginary portion of a complex number and Re may correspond to a real portion of the complex number. The $\Phi$ term may correspond to a phase difference between wave fronts $u_1$ (unsheared) and $u_2$ (sheared). This phase difference $\Phi$ may correspond to an unloaded, non-deformed, and/or reference state of test object. To calculate strain, it may be desirable to compare reference phase difference $\Phi$ with a loaded, deformed, and/or testing phase difference $\Phi'$.

In embodiments, a testing phase difference $\Phi'$ may be obtained by similar operations as applied to obtain reference phase difference $\Phi$. For example, a Fourier transform may be applied to an intensity equation of a second image (e.g., corresponding to a test object 50 in second state 54) and a WIFT may be applied to the resulting spectrum to obtain the testing phase difference Φ'. The relative phase difference ΔΦ between the reference and loaded test object may be represented as:

$$\Delta\Phi = \Phi - \Phi'$$ Eq. 7.

Figure 3:
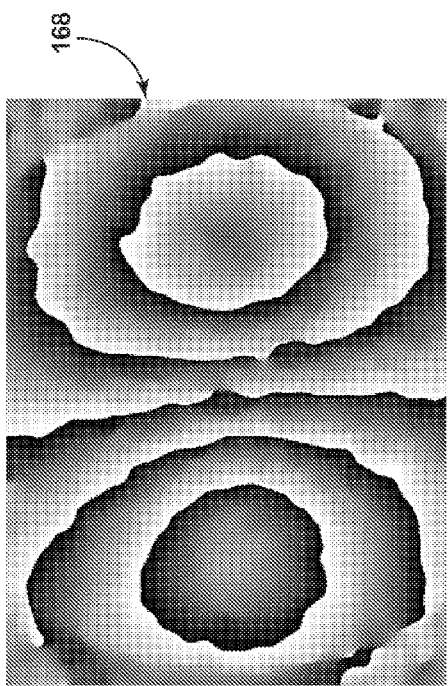
FIG. 3 is a phase map corresponding to an embodiment of a shearography system in accordance with teachings of the present disclosure.

FIG. 3 generally illustrates a phase map 168 corresponding to the phase difference calculated in Eq. 7. A gradient of deformation may be calculated according to:

$$\Delta\Phi = \frac{2\pi \cdot \Delta x}{\lambda} d \cdot s.$$ Eq. 8 where, Δx corresponds to a shearing amount, d may correspond to an x component $$\left(\text{e.g., } \frac{\partial u}{\partial x}\right)$$

of a gradient of deformation vector, $$d = \left(\frac{\partial u}{\partial x}, \frac{\partial v}{\partial x}, \frac{\partial w}{\partial x}\right) = .$$

The s term may correspond to a sensitivity vector, which may correspond to $s = k_i - k_0$. The $k_i$ term may correspond to a unit vector along the illumination direction and $k_0$ may correspond to a unit vector in the observation direction. Thus, s may be represented according to:

$$s = (\sin \theta, 0, 1 + \cos \alpha)$$ Eq. 9.

where θ corresponds to an illumination angle. Equation 8 may be solved for $$\frac{\partial u}{\partial x}$$

to determine strain in the x-direction.

In embodiments, it may be desirable for a speckle to cover at least six pixels. In embodiments, it may also be desirable to increase spatial resolution to attempt to achieve or to achieve an ideal spectrum, which may allow for easier and/or more accurate extraction of phase information. Larger speckle size may reduce spatial resolution, so it may be desirable to reduce the size of the pixels so that a relatively small speckle may still be able to cover at least six pixels.

Figure 4B:
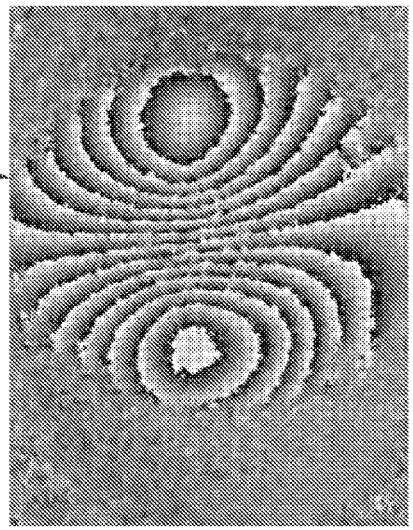
FIGS. 4A and 4B are phase maps corresponding to embodiments of a shearography system in accordance with teachings of the present disclosure.
Figure 4A:
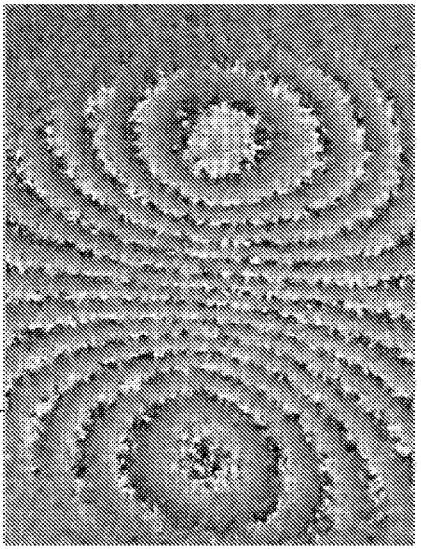

In embodiments, a high resolution camera may include a relatively small pixel size, which may help limit the size of the speckles. For example, a 5 Megapixel camera (e.g., a model ICL-B2520M camera available from IMPERX) may include about 2456 pixels by about 2058 pixels, with a pixel size of about 3.4 μm, and a 1.5 Megapixel camera (e.g., a model STC-CL152A available from SENTECH) may include about 1392 pixels by about 1040 pixels, with a pixel size of about 4.7 μm. The reduced pixel size of the 5 Megapixel camera may allow for a reduced speckle size Δs and increased spatial resolution. In embodiments, the difference between a phase map generated via a 1.5 Megapixel camera (e.g., as generally illustrated in FIG. 4A) and a phase map generated via a 5 Megapixel camera (e.g., as generally illustrated in FIG. 4B) may be significant.

In embodiments, the focus length $L_f$ may affect the speckle size. For example, the speckle size may be represented by:

$$\Delta s = \lambda_1 L_f / D$$ Eq. 10.

where Δs corresponds to the speckle size, $\lambda_1$ corresponds to the wavelength of first light source, $L_f$ corresponds to the focus length of an imaging lens and D corresponds to the aperture size. Thus, as focus length $L_f$ decreases, speckle size Δs may also decrease, proportionately.

Figure 5:
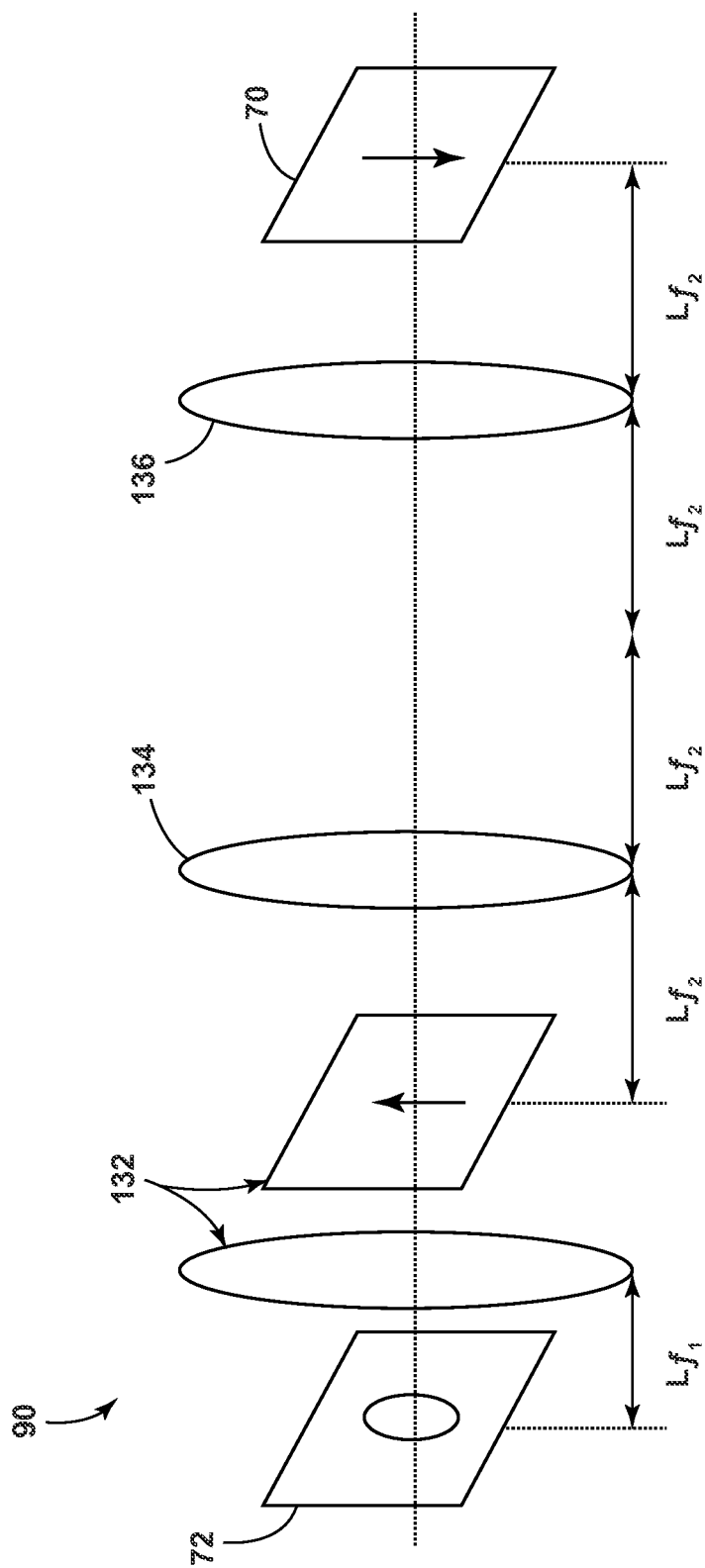
FIG. 5 is a schematic of a lens configuration of an embodiment of a shearography system in accordance with teachings of the present disclosure.
Figure 8A:
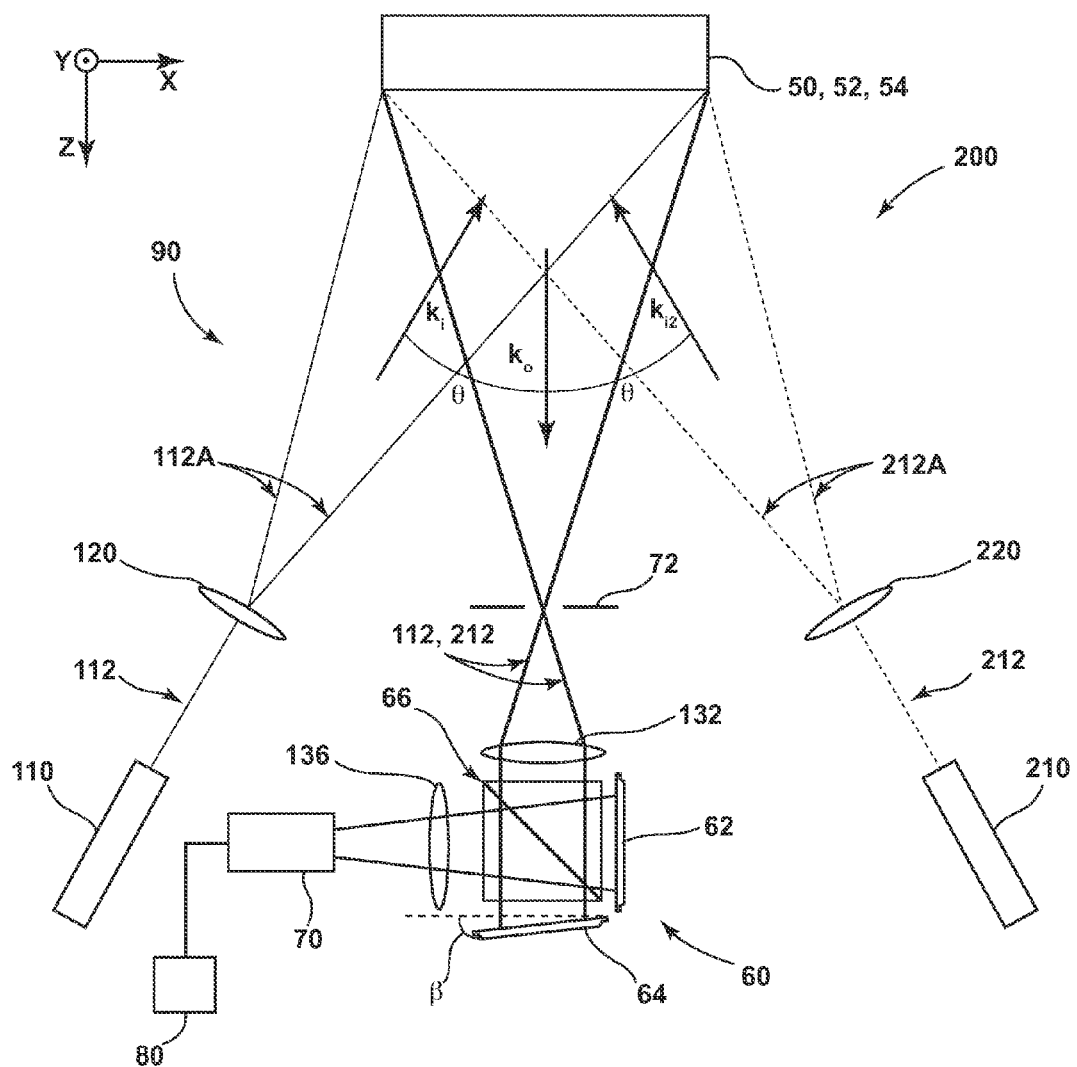
FIG. 8A is a schematic view of an embodiment of a shearography system in accordance with teachings of the present disclosure.

In embodiments, focus length $L_f$ may be relatively short compared to a conventional Mach-Zehdner Interferometer. In embodiments of a shearography system (e.g., system 100 and/or system 200), additional lenses may be included to increase a field of view of a test object. For example, as generally illustrated in FIGS. 1A, 5 and 8A, embodiments may include lens 134 and/or lens 136. Image lens 132 may include a focus length of $L_{f1}$ and lenses 134 and 136 may include a focus length of $L_{f2}$. As generally shown in FIG. 5, which generally illustrates an unfolded schematic of a lens configuration of an embodiment, added lenses 134 and 136 may correspond to a 4f system that may include a magnification ratio of −1. A magnification ratio of −1 that may correspond to the added lenses may flip the image upside down, but may not affect the speckle size Δs.

Aperture 72 may be located between test object 50 and optical shearing device 60. In practical applications of embodiments, certain variables may be relatively fixed and/or constrained (e.g., maximum resolution of CCD camera, focus length, etc.), and the configuration of aperture 72 may be controlled to achieve certain desired system effects. For example, the size D of aperture 72 may be adjusted to control the speckle size in the system. In embodiments, the size D of aperture may be increased to decrease speckle size Δs and/or the size D of aperture may be decreased to increase speckle size Δs.

Additionally or alternatively, the size D of aperture 72 may be configured to act as a spatial frequency filter, which may limit a maximum spatial frequency that can be captured (e.g., the size of the aperture may correspond to a cutoff spatial frequency). A relationship between the size of aperture and the cutoff spatial frequency may include:

$$f_{c1} = D/2\lambda_1 L_f$$ Eq. 11.

where $f_{c1}$ corresponds to a cutoff spatial frequency, D corresponds to aperture size (e.g., a diameter) on a focus plane, $\lambda_1$ corresponds to a wavelength of first light source 112 and $L_f$ corresponds to a focus length of image lens 132.

In embodiments, a sufficiently large spatial frequency shift $f_0$ may make it easier and/or possible to separate various portions of spectrum from each other in the frequency domain. In embodiments, it may be desirable to include a spatial frequency shift $f_0$ that is at least twice the cutoff frequency $f_c$. Thus, it may be desirable for the following relationship to be true:

$$2f_{c1} \leq f_0 = \frac{\sin\beta}{\lambda_1}.$$ Eq. 12

Thus, it may be desirable to introduce shearing angle β according to the following relationship:

$$\arcsin\left(\frac{D}{L_f}\right) \leq \beta.$$ Eq. 13

The relationship of Equation 13 may be derived from Equations 3, 11, and 12.

In embodiments, a spatial frequency shift $f_0$ may be introduced by disposing at least one of the mirrors of an interferometer (e.g., mirror 64) in an orientation corresponding to the shearing angle β. Shearing angle β may also have a maximum desired value, which may correspond to the maximum spatial frequency that can be captured by camera 70. A maximum spatial frequency that may be captured by a camera may correspond to one half of the pixel size of the camera. A maximum desired value of shearing angle β may be determined according to:

$$f_0 = \frac{\sin\beta}{\lambda_1} \leq \frac{2f_{max}}{3} = \left(\frac{1}{3\Delta}\right). \quad \text{Eq. 14}$$

Equation 14 may also be represented as:

$$\beta \leq \arcsin\left(\frac{\lambda}{3\Delta}\right). \quad \text{Eq. 15}$$

Thus, it may be desirable if the shearing angle β satisfies the following:

$$\beta \in \left[\arcsin\left(\frac{D}{L_f}\right), \arcsin\left(\frac{\lambda}{3\Delta}\right)\right]. \quad \text{Eq. 16}$$

Equation 16 may also be represented as:

$$D \leq L_f \sin\beta \leq \frac{\lambda L_f}{3\Delta}. \quad \text{Eq. 17}$$

In embodiments, increasing aperture size D as much as possible may provide a greater signal to noise (S/N) ratio, which may be desirable. As the S/N ratio increases, it may be possible to use a greater portion of spectrum 150 resulting from the Fourier transformation. However, it may be desirable to configure aperture size D to accommodate for increased speckle size Δs (e.g., Eq. 10) and non-frequency aliasing (e.g., Eq. 16). A smaller aperture size D may correspond to increased speckle size Δs, and/or may prevent and/or reduce non-frequency aliasing.

In embodiments, it may be desirable to configure aperture size D to balance improving signal-to-noise ratio S/N with increasing speckle size Δs and/or with reducing non-frequency aliasing. For example, in embodiments, shearing angle β may be determined first according to a desired measurement sensitivity, as measurement sensitivity may be proportional to the shearing angle β. Once shearing angle β is selected, the largest aperture size D permitted according to Equation 17 may be selected to achieve as high of a S/N ratio as possible.

In embodiments, system may include one or more WIFT filters 170. WIFT filter 170 may be configured to extract and/or filter phase information from a spectrum, such as, for example, a spectrum corresponding to a Fourier transform of an image. It may be desirable to configure an algorithm of WIFT filter 170 to be relatively simple so that the algorithm may be carried out relatively quickly, which may allow for use of WIFT filter 170 in conjunction with dynamic measurements.

Figure 6B:
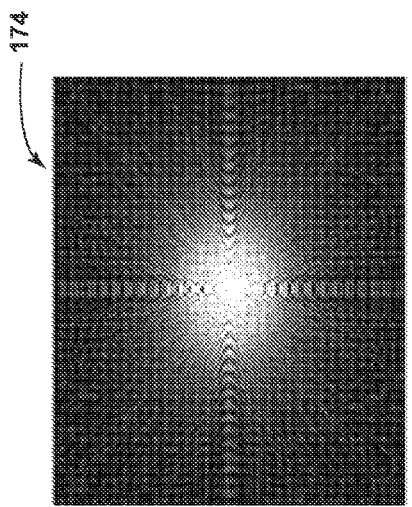
FIG. 6B is a graphical representation of an inverse Fourier transformed gate function of an embodiment of a shearography system in accordance with teachings of the present disclosure.
Figure 6A:
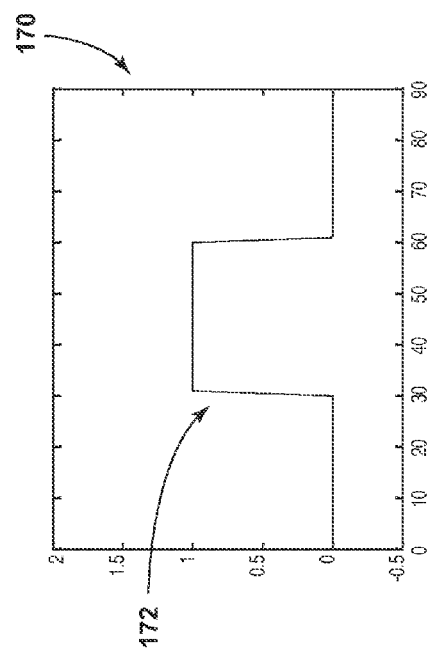
FIG. 6A is a graphical representation of a gate function of an embodiment of a shearography system in accordance with teachings of the present disclosure.

In embodiments, WIFT filter 170 may comprise a gate function 172. A plot of a gate function 172 is generally illustrated in FIG. 6(a) and an inverse Fourier transformed gate function 174 is generally illustrated in FIG. 6(b).

In embodiments, WIFT filter 170 may comprise a normal function filter, which may be represented as:

$$\varphi(x, y) = \frac{1}{2\pi\sigma_x\sigma_y} e^{-\frac{1}{2}\left[\frac{(x-\mu_x)^2}{\sigma_x^2} + \frac{(y-\mu_y)^2}{\sigma_y^2}\right]}. \quad \text{Eq. 18}$$

Figure 7B:
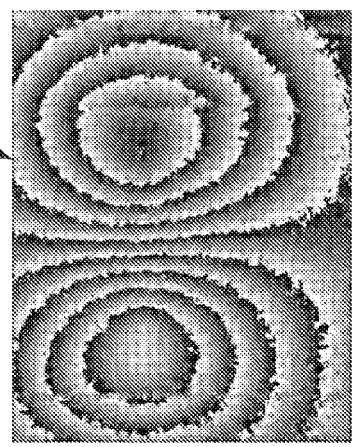
FIGS. 7A and 7B are phase maps corresponding to embodiments of a shearography system in accordance with teachings of the present disclosure.
Figure 7A:
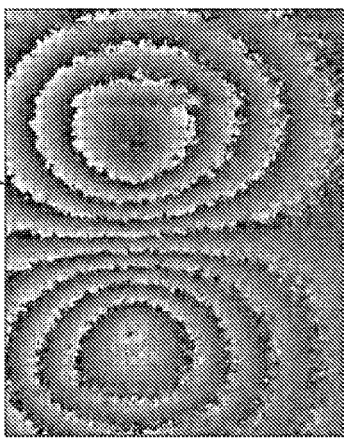

As the inverse Fourier transformation of a normal function (e.g., a normal function filter) may still be a normal function, a WIFT filter 170 comprising a normal function filter may not introduce extra fringes and/or as many extra fringes as embodiments in which WIFT filter 170 comprises a gate function. As generally illustrated in FIGS. 7A and 7B, a WIFT filter 170 comprising a normal function filter (e.g., as generally illustrated in FIG. 7B) may result in a phase map 168D with less noise than a phase map 168C resulting from a WIFT filter comprising a gate function (e.g., as generally illustrated in FIG. 7A).

Figure 8B:
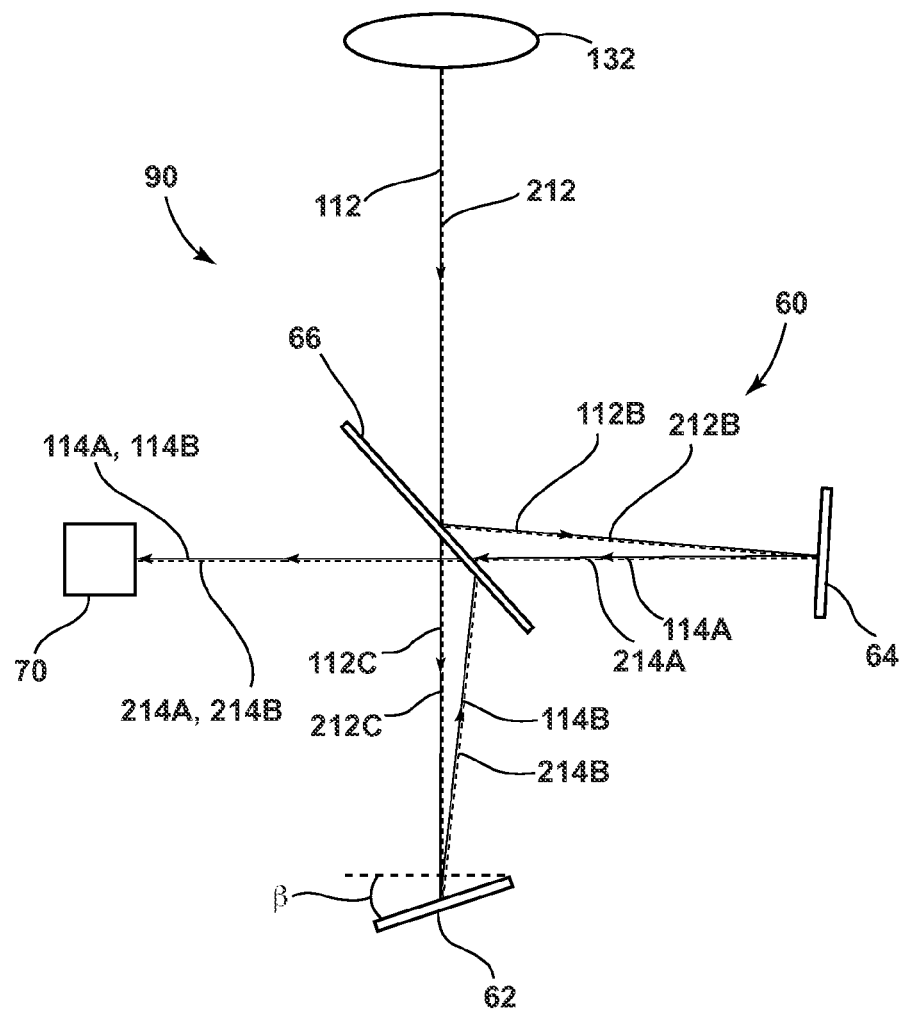
FIG. 8B is a schematic view of portions of an embodiment of a shearography system in accordance with teachings of the present disclosure.

As generally illustrated in FIGS. 8A and 8B, embodiments of a shearography system (e.g., shearography system 200) may include multiple light sources (e.g., first light source 110 and second light source 210). In embodiments, shearography system 200 may be similar to and/or include a similar configuration as that shown and/or described in connection with shearography system 100, as generally illustrated in FIG. 1A. For example, and without limitation, shearography system 200 may include first light source 110, optical shearing device 60, camera 70, and/or aperture 72.

In embodiments, shearography system 200 may include a second light source 210. Second light source 210 may be configured to provide a second light and/or laser, which may include a second wavelength. In embodiments, first wavelength of first light source 110 and second wavelength of second light source 210 may be equal or may be unequal. Second light source 210 may be disposed on an opposite side of optical shearing device 70 relative to first light source 110 (e.g., first light source and second light source 210 may be separated by about 180 degrees when viewed from test object 50). Second light source 210 may be configured to illuminate (e.g., direct a second beam 212 toward) test object 50. In embodiments, first light source 110 and second light source 210 may be configured to simultaneously illuminate test object 50 test object. In embodiments, second beam 212 may be expanded into an expanded second beam 212A via a second beam expander 220. In embodiments, first and second light sources 110, 210 may be configured to direct first beam 112 and second beam 212, respectively, toward the same location and/or area of test object 50 (e.g., illuminate test object 50). In embodiments, first and second light sources 110, 210 may be configured to simultaneously direct first beam 112 and second beam 212, respectively, toward the same location and/or area of test object 50 (e.g., simultaneously illuminate test object 50). In embodiments, it may be desirable for first wavelength $\lambda_1$ and the second wavelength $\lambda_2$ to be unequal, which may reduce and/or eliminate interference between first light source 110 and second light source 210 (e.g., relative to the first and second wavelengths being equal). In embodiments, first light source 110 and second light source 210 may be aligned with each other or, as generally illustrated in FIG. 8A, first light source 110 and second light source 210 may be aligned opposite each other (e.g., about 180 degrees apart if viewed from testing object 50).

In embodiments, shearography system 200 may allow for simultaneously measuring individual components (e.g., in the x-direction, in the y-direction, and/or the z-direction) of strain. Camera 70 may be configured to obtain intensity information corresponding to interferograms of sheared and unsheared versions of beams of light (e.g., first beam 112 and second beam 212). Intensity information may then be used to determine phase difference information between loaded and unloaded states of test object 50 for the first beam 112 and/or the second beam 212. Phase difference information may then be used to calculate strain, which may include calculating individual components of pure in-plane normal strain, pure in-plane shear strain, and pure out-of-plane shear strain.

In embodiments, first beam expander 120 may be configured to expand first beam 112, which may result in illumination of a larger area of test object 50. In embodiments, second beam expander 220 may be configured to expand second beam 212, which may result in illumination of a larger area of test object 50 (e.g., relative to second beam 212 illuminating test object 50 without second beam expander 220). First and second beams 112, 212 may illuminate generally the same area of testing object. First beam 112 and/or second beam 212 may reflect off of testing object 50 in a direction toward aperture 72.

In embodiments, a mirror (e.g., mirror 62 and/or mirror 64) may be tilted to introduce a first frequency component $f_1$ to first beam 112 and/or a second frequency component $f_2$ to second beam 212. The introduction of a frequency component may be referred to as shearing. First and second spatial frequency components $f_1$, $f_2$ may be represented, respectively, as:

$$f_1 = (\sin \beta/\lambda_1) \quad \text{Eq. 19.}$$

$$f_2 = (\sin \beta/\lambda_2) \quad \text{Eq. 20.}$$

where β corresponds to the shearing angle (e.g., the tilting angle of mirror 64), $\lambda_1$ corresponds to a wavelength of first light source, and $\lambda_2$ corresponds to a wavelength of second light source. Thus, an introduced spatial frequency components (e.g., $f_1$, $f_2$) may correspond to a ratio of the shearing angle β and the wavelength (e.g., $\lambda_1$, $\lambda_2$) of the respective light source.

In embodiments, a plurality of wave fronts may result from optical shearing device 60. For example, in embodiments, first wave front 114A may correspond to (e.g., originate from) the $k_{i1}$ direction and/or first light source 110, and/or may reflect off of mirror 62, and may be represented by the following equation:

$$u_{11}(x,y) = |u_{11}(x,y)| \exp[i\varphi_1(x,y)] \quad \text{Eq. 21.}$$

In embodiments, second wave front 114B may correspond to the $k_{r1}$ direction, first light source 110, and/or mirror 64, and may be represented by the following equation:

$$u_{12}(x,y) = |u_{12}(x+\Delta x,y)| \exp\{i\varphi_1(x+\Delta x,y) + 2\pi i f_1 \cdot x\} \quad \text{Eq. 22.}$$

In embodiments, a third wave front 214A corresponding to the $k_{i2}$ direction, second light source 210, and/or mirror 62 may be represented by the following equation:

$$u_{21}(x,y) = |u_{21}(x,y)| \exp[i\varphi_2(x,y)] \quad \text{Eq. 23.}$$

In embodiments, a fourth wave front 214B corresponding to the $k_{r2}$ direction, second light source 210, and/or mirror 64 may be represented by the following equation:

$$u_{22}(x,y) = |u_{22}(x+\Delta x,y)| \exp\{i\varphi_2(x+\Delta x,y) + 2\pi i f_2 \cdot x\} \quad \text{Eq. 24.}$$

Camera 70 may be configured to detect, receive, capture, and/or measure the light and/or the intensity of the light output from optical shearing device 60, such as, for example, wavefronts 114A, 114B, 214A, 214B, which may include light reflections corresponding to first light source 110 and/or second light source 210. In embodiments, camera 70 may be configured to obtain intensity information while first light source 110 and second light source 210 are simultaneously illuminating test object 50. For example, camera 70 may be configured to record the intensity of wavefronts 114A, 114B, 214A, 214B. In embodiments, a recorded intensity may be represented by:

$$\begin{aligned} I &= (u_{11}+u_{12})(u_{11}^*+u_{12}^*) + (u_{21}+u_{22})(u_{21}^*+u_{22}^*) \\ &= (u_{11}u_{11}^* + u_{12}u_{12}^* + u_{11}u_{12}^* + u_{12}u_{11}^*) + \\ &\quad (u_{21}u_{21}^* + u_{22}u_{22}^* + u_{21}u_{22}^* + u_{22}u_{21}^*) \\ &= (u_{11}u_{11}^* + u_{12}u_{12}^*) + (u_{21}u_{21}^* + u_{22}u_{22}^*) + \\ &\quad (u_{11}u_{12}^* + u_{12}u_{11}^*) + (u_{21}u_{22}^* + u_{22}u_{21}^*). \end{aligned} \quad \text{Eq. 25}$$

where * corresponds to a complex conjugate of $u_i$ (e.g., $u_1^*$ corresponds to a complex conjugate of $u_1$).

The recorded intensity may be processed by processing unit 80. For example, and without limitation, camera 70 may be configured generate one or more electrical signals corresponding to measured intensity and processing unit 80 may be configured to receive and/or process the signal or signals. Processing unit 80 may be configured to apply a Fourier transform to an intensity information (e.g., Equation 25). The result of a Fourier transform applied to Equation 25 may be represented by:

$$\begin{aligned} FT(I) = &[U_{11}(f_x, f_y) \otimes U_{11}^*(f_x, f_y) + \\ &U_{12}(f_x+f_1, f_y) \otimes U_{12}^*(f_x+f_1, f_y)] + \\ &[U_{21}(f_x, f_y) \otimes U_{21}^*(f_x, f_y) + \\ &U_{22}(f_x+f_2, f_y) \otimes U_{22}^*(f_x+f_2, f_y)] + \\ &[U_{11}(f_x, f_y) \otimes U_{12}^*(f_x+f_1, f_y) + \\ &U_{12}(f_x+f_1, f_y) \otimes U_{11}^*(f_x, f_y)] + \\ &[U_{21}(f_x, f_y) \otimes U_{22}^*(f_x+f_2, f_y) + \\ &U_{22}(f_x+f_2, f_y) \otimes U_{21}^*(f_x, f_y)]. \end{aligned} \quad \text{Eq. 26}$$

where $\otimes$ is the convolution operation, $U_{11}(f_x, f_y)$=FT$(u_{11})$, $U_{12}(f_x+f_1, f_y)$=FT$(u_{12})$, $U_{21}(f_x, f_y)$=FT$(u_{21})$, $U_{22}(f_x+f_2, f_y)$=FT$(u_{22})$.

Figure 9:
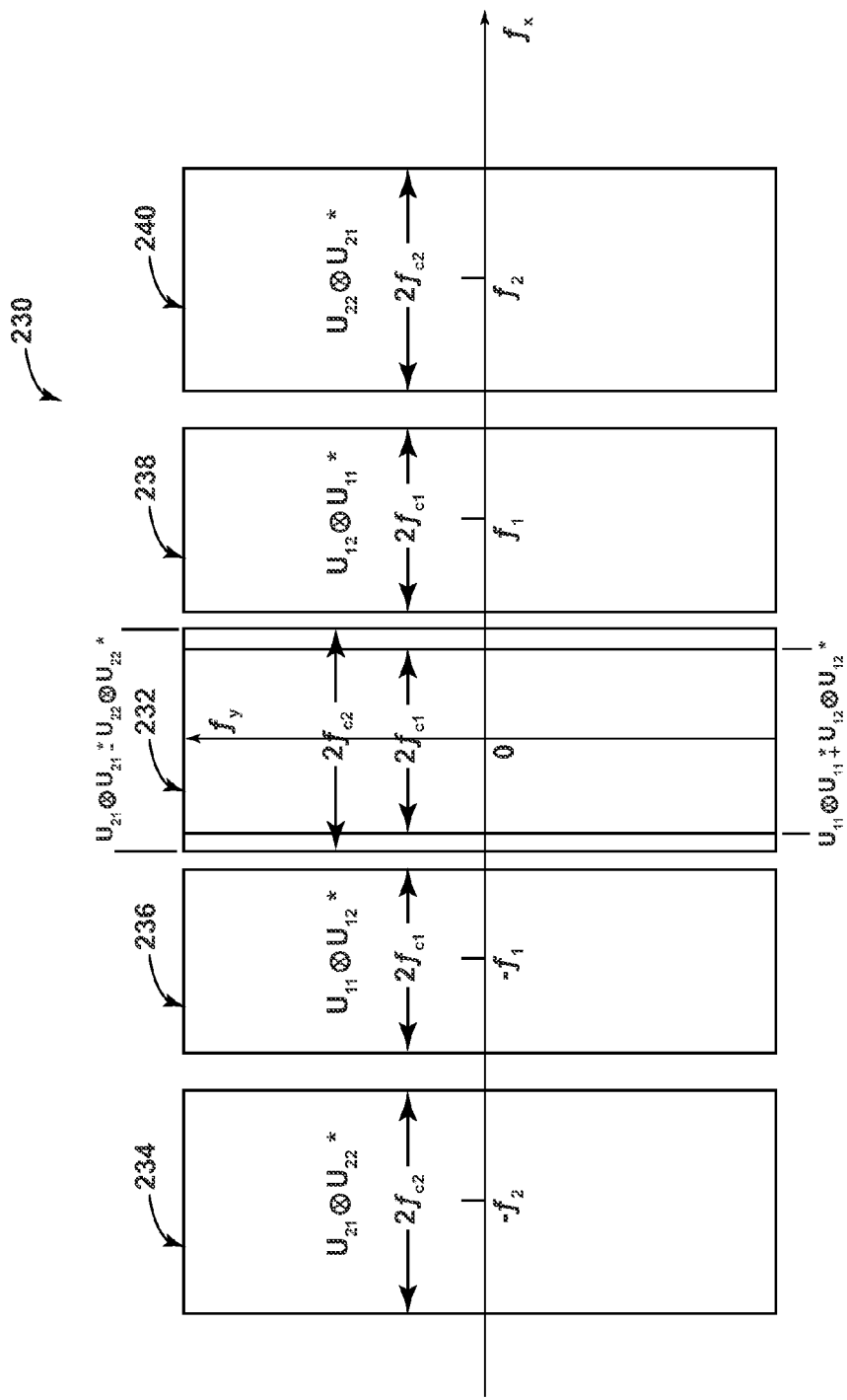
FIG. 9 is a spectrum corresponding to an embodiment of a shearography system in accordance with teachings of the present disclosure.

In embodiments, as generally illustrated in FIG. 9, a Fourier transform may result in spectrum 230, which may correspond to the recorded intensity. Spectrum 230 may include a plurality of spectra that may correspond to the Fourier transform of the captured intensity (e.g., the terms of Equation 26). Differing spatial frequencies may separate the spectra into a plurality of parts. For example, and without limitation, the $U_{11} \otimes U_{11}^* + U_{12} \otimes U_{12}^*$ term and/or the $U_{21} \otimes U_{21}^* + U_{22} \otimes U_{22}^*$ term, which may correspond to low frequency terms, may be located at or near the center portion 232 of spectrum 230. The $U_{11} \otimes U_{11}^* + U_{12} \otimes U_{12}^*$ term may include a width of $2f_{c1}$ and/or the $U_{21} \otimes U_{21}^* + U_{22} \otimes U_{22}^*$ term may include a width of $2f_{c2}$. The $U_{11} \otimes U_{11}^* + U_{12} \otimes U_{12}^*$ term and/or the $U_{21} \otimes U_{21}^* + U_{22} \otimes U_{22}^*$ term may correspond to background light and may not contain desired information (e.g., may not contain desired phase information).

In embodiments, the remaining terms may include phase information. The $U_{12} \otimes U_{11}^*$ term may correspond to portion 238 of spectrum 230, which may be located at or near ($f_1$, 0). The $U_{12} \otimes U_{11}^*$ term may correspond to portion 236 of spectrum 230, which may be located at or near ($-f_1$, 0). The $U_{12} \otimes U_{11}^*$ and $U_{12} \otimes U_{11}^*$ terms may each include/correspond to a spectrum width of $2f_{c1}$. These two terms may include phase information of the recorded speckle interferogram in the $k_{i1}$ direction.

The $U_{22} \otimes U_{21}^*$ term may correspond to portion 240 of spectrum 230, which may be located at or near ($f_2$, 0). The $U_{21} \otimes U_{22}^*$ term may correspond to portion 234 of spectrum 230, which may be located at or near ($-f_2$, 0). The $U_{22} \otimes U_{21}^*$ term and/or the $U_{21} \otimes U_{22}^*$ term may correspond to a spectrum width of $2f_{c2}$. One or both of the $U_{22} \otimes U_{21}^*$ term and/or the $U_{21} \otimes U_{22}^*$ term may include phase information related to the recorded speckle interferogram in the $k_{i2}$ direction.

In embodiments, values of cutoff frequencies $f_{c1}$ and $f_{c2}$ may correspond to the size of aperture D. For example, and without limitation, $$f_{c1} = D/2\lambda_1 L_f \qquad \text{Eq. 27.}$$

$$f_{c2} = D/2\lambda_2 L_f \qquad \text{Eq. 28.}$$

where D corresponds to an aperture size (e.g., a diameter) on a focus plane, $\lambda_1$ corresponds to a wavelength of first light source 112, $\lambda_2$ corresponds to a wavelength of second light source 212, and $L_f$ corresponds to a focus length of image lens 132.

A Windowed Inverse Fourier Transform (WIFT) may be applied to the Fourier transformed intensity information. In embodiments, a first window of the windowed inverse Fourier transform may correspond to (e.g., be centered at) frequency component $f_1$ which may correspond to the wavelength of first beam 112 and the shearing angle (see, e.g., Equation 19) and/or the first window may include a width of $2f_{c1}$. A second window of the windowed inverse Fourier transform may correspond to frequency component $f_2$ which may correspond to the wavelength of second beam 212 and the shearing angle (see, e.g., Equation 20), and/or the second window may include a width of $2f_{c2}$. Applying a WIFT to the Fourier transformed intensity information (e.g., to spectrum portion 238 and/or spectrum portion 240) may allow for the phase information (e.g., distributions) to be determined, such as via the complex amplitudes. For example, applying a WIFT to a Fourier transformed captured intensity may result in the following:

$$[\phi_1 + 2\pi x f_1] = \arctan \frac{\operatorname{Im}[u_{12} u_{11}^*]}{\operatorname{Re}[u_{12} u_{11}^*]}. \qquad \text{Eq. 29}$$

$$[\phi_2 + 2\pi x f_2] = \arctan \frac{\operatorname{Im}[u_{22} u_{21}^*]}{\operatorname{Re}[u_{22} u_{21}^*]}. \qquad \text{Eq. 30}$$

where Im and Re correspond to the imaginary and real part of the complex numbers, respectively. In embodiments, $\phi_i$ may correspond to a phase difference between a sheared portion of a beam and an unsheared portion of a beam. In embodiments, $\phi_1$ may correspond to a phase difference between first (e.g., unsheared) portion of first beam ($\varphi_1(x, y)$) and second (e.g., sheared) portion of first beam ($\varphi_1(x + \Delta x, y)$):

$$\phi_1 = \varphi_1(x,y) - \varphi_1(x+\Delta x, y) \qquad \text{Eq. 31.}$$

In embodiments, $\phi_2$ may correspond to a phase difference between first (e.g., unsheared) portion 212B of second beam 212 ($\varphi_2(x, y)$) and second (e.g., sheared) portion 212C of second beam 212 ($\varphi_2(x+\Delta x, y)$):

$$\phi_2 = \varphi_2(x,y) - \varphi_2(x+\Delta x, y) \qquad \text{Eq. 32.}$$

Phase differences $\phi_1$ and $\phi_2$ may correspond to a reference state 52 of test object 50.

In embodiments, a second measurement may, additionally or alternatively, be taken for second state 54 of test object 50. A second measurement may be similar to the reference measurement. For example, applying a Fourier transform to the captured intensity from object 50 in second state 54 and then applying a WIFT may result in the following:

$$[\phi_1' + 2\pi x f_1] = \arctan \frac{\operatorname{Im}[u_{12} u_{11}^*]}{\operatorname{Re}[u_{12} u_{11}^*]}. \qquad \text{Eq. 33}$$

$$[\phi_2' + 2\pi x f_2] = \arctan \frac{\operatorname{Im}[u_{22} u_{21}^*]}{\operatorname{Re}[u_{22} u_{21}^*]}. \qquad \text{Eq. 34}$$

where $\phi_1'$ and $\phi_2'$ represent the phase differences corresponding to the second state 54 (e.g., a testing state) of test object 50. A first relative phase difference $\Delta_1$ may be calculated for light corresponding to first light source $\phi_1'$ (second state 54) and $\phi_1$ (first state 52) and/or a second relative phase difference $\Delta_2$ may be calculated for light corresponding to second light source $\phi_2'$ (second state 54) and $\phi_2$ (first state 52).

$$\Delta_1 = \phi_1' - \phi_1 \qquad \text{Eq. 35.}$$

$$\Delta_2 = \phi_2' - \phi_2 \qquad \text{Eq. 36.}$$

Relative phase differences $\Delta_1$ and/or $\Delta_2$ may correspond to the deformation and/or gradient of deformation, if any, of test object 50 in second state 54 relative to test object 50 in first state 52. Based on the relationship between relative phase difference and strain, Equations 35 and 36 may be solved to obtain at least two strain components. For example, and without limitation, for a configuration including x, z illumination and shearing in the x-direction (e.g., via second mirror 64 tilting with respect to the x axis, such as generally illustrated in FIG. 1A), unknowns terms $$\frac{\partial u}{\partial x}$$

(pure normal in-plane strain) and $$\frac{\partial w}{\partial x}$$

(pure shear out-of-plane strain) may be solved for via the following equations:

$$\Delta_1 = \frac{2\pi \Delta x}{\lambda_1}\left\{\frac{\partial u}{\partial x}\sin(+\theta) + \frac{\partial w}{\partial x}[1+\cos(+\theta)]\right\}. \quad \text{Eq. 37}$$

$$\Delta_2 = \frac{2\pi \Delta x}{\lambda_2}\left\{\frac{\partial u}{\partial x}\sin(-\theta) + \frac{\partial w}{\partial x}[1+\cos(-\theta)]\right\}. \quad \text{Eq. 38}$$

where θ corresponds to an illumination angle. Equations 37 and 38 may then result in the following equation that may be solved/computed (e.g., all of $\lambda_1$, $\lambda_2$, $\Delta_1$, $\Delta_2$, and $\Delta x$ are known) for pure in-plane strain in the x-direction:

$$\frac{\partial u}{\partial x} = \frac{\lambda_1\Delta_1 - \lambda_2\Delta_2}{4\pi\Delta x}(x, z \text{ plane illumination shearing in } x). \quad \text{Eq. 39}$$

A similar calculation may be used to determine $$\frac{\partial w}{\partial x}$$

and/or the calculated $$\frac{\partial u}{\partial x}$$

may be inserted into Equation 37 or Equation 38. Thus, via a single setup/configuration, pure in-plane normal strain and pure out-of-plane shear strain may be calculated. If the illumination plane is changed to the y-z plane (e.g., via rotating first light source 110 and second light source 210 in a clockwise or counterclockwise direction 90 degrees), a y-direction component of pure in-plane shear strain with shearing in the x-direction may be calculated via the following equation:

$$\frac{\partial v}{\partial x} = \frac{\lambda_1\Delta_1 - \lambda_2\Delta_2}{4\pi\Delta x}(y, z \text{ plane illumination shearing in } x). \quad \text{Eq. 40}$$

In embodiments, a shearing direction may be changed. For example, and without limitation, the following equations may correspond to changes in shearing direction. An x-direction component of pure in-plane shear strain, $$\frac{\partial u}{\partial y},$$

with shearing in the y-direction (e.g., via tilting second mirror 64 with respect to the y-axis), may be determined from the following equation:

$$\frac{\partial u}{\partial y} = \frac{\lambda_1\Delta_1 - \lambda_2\Delta_2}{4\pi\Delta y}(x, z \text{ plane illumination shearing in } y). \quad \text{Eq. 41}$$

A y-direction component of pure in-plane normal strain may be calculated via the following equation:

$$\frac{\partial v}{\partial y} = \frac{\lambda_1\Delta_1 - \lambda_2\Delta_2}{4\pi\Delta y}(y, z \text{ plane illumination shearing in } y). \quad \text{Eq. 42}$$

If the shearing direction is changed to the y-direction, a y-component of pure out-of-plane shear strain, $$\frac{\partial w}{\partial y},$$

may be calculated similarly to the calculation of $$\frac{\partial w}{\partial x}$$

above.

Figure 10:
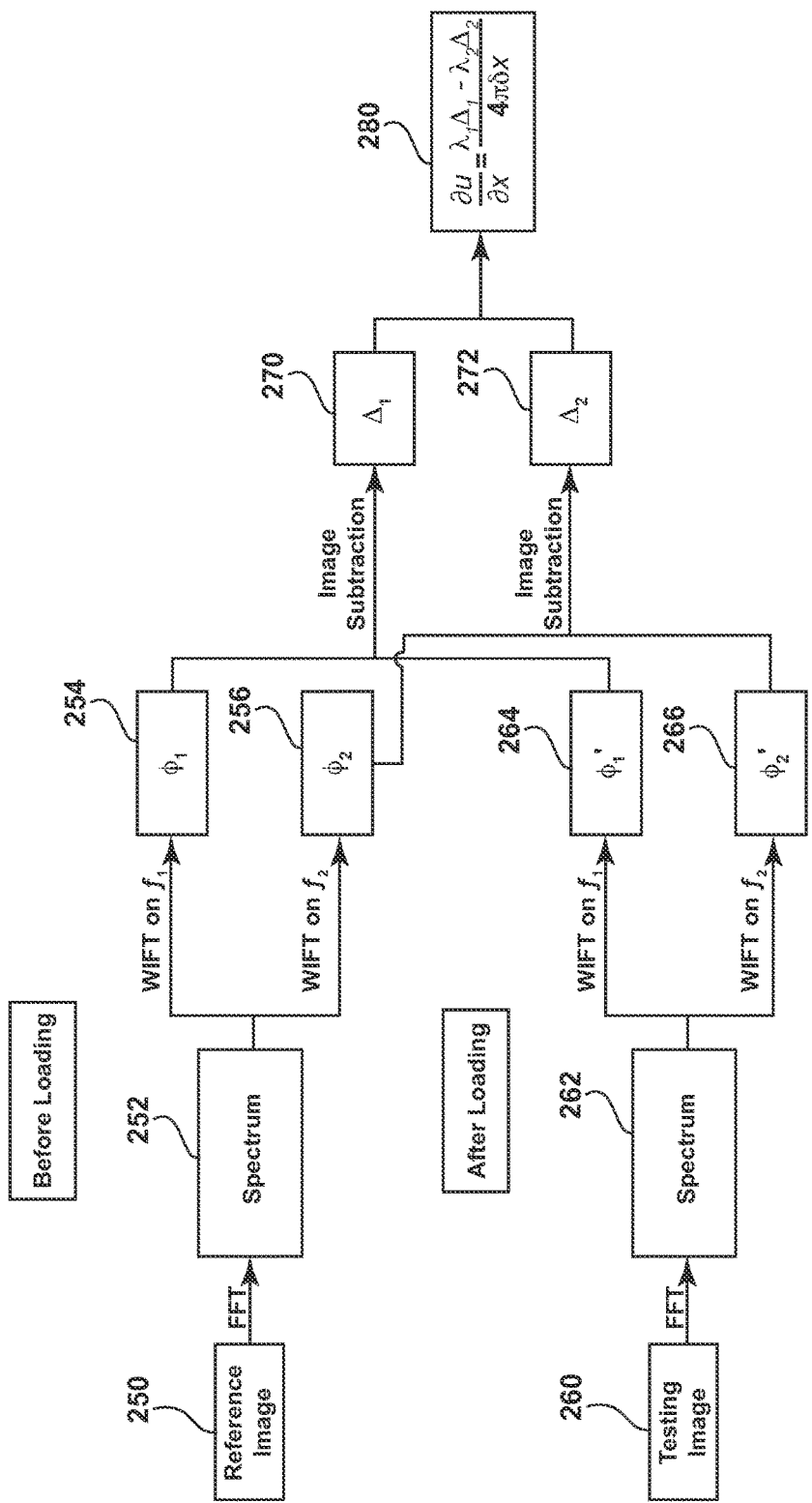
FIG. 10 is a block diagram of a method of determining strain according to an embodiment of the present disclosure.

An exemplary schematic of a method of measuring strain conducted in embodiments of a shearography system (e.g., shearography system 200) is generally illustrated in FIG. 10. In step 250, reference information (e.g., reference intensity information and/or a reference image), which may include one or more spatial frequency components, may be acquired for a test object 50 in first state 52 by camera 70. In step 252, a Fourier transform may then be applied to the reference information and a reference spectrum may be generated from the Fourier transformed reference information. In step 254, a WIFT filter may be applied to the Fourier transformed reference information and/or spectrum according to the one or more spatial frequency components to obtain a reference phase difference or reference phase differences. For example, and without limitation, a first WIFT, which may correspond to spatial frequency component $f_1$, and a second WIFT, which may correspond to spatial frequency component $f_2$, may be applied to the reference spectrum.

In embodiments, test object 50 may then be loaded and, in step 260, testing information (e.g., testing intensity information and/or a testing image), which may include one or more spatial frequency components, may be acquired of the loaded test object 50 via camera 70. In step 262, a Fourier transform may then be applied to the testing image (loaded) to obtain a testing spectrum. In step 264 and/or step 266, a WIFT may be applied to the testing information and/or spectrum according to the one or more spatial frequency components to obtain a testing phase difference or testing phase differences for the loaded test object. For example, and without limitation, a first WIFT, which may correspond to spatial frequency component $f_1$, and a second WIFT, which may correspond to spatial frequency component $f_2$, may be applied to the testing spectrum.

In steps 270 and 272, relative differences between phase differences corresponding to each spatial frequency component may then be determined with respect to the reference information and the testing information. For example, and without limitation, a difference between phase difference $\phi_1$ and phase difference $\phi_1'$ may correspond to frequency component $f_1$, and/or a difference between phase difference $\phi_2$ vs. $\phi_2'$ may correspond to frequency component $f_2$. In step 280, a strain measurement may then be determined from the relative phase differences.

Figure 11A:
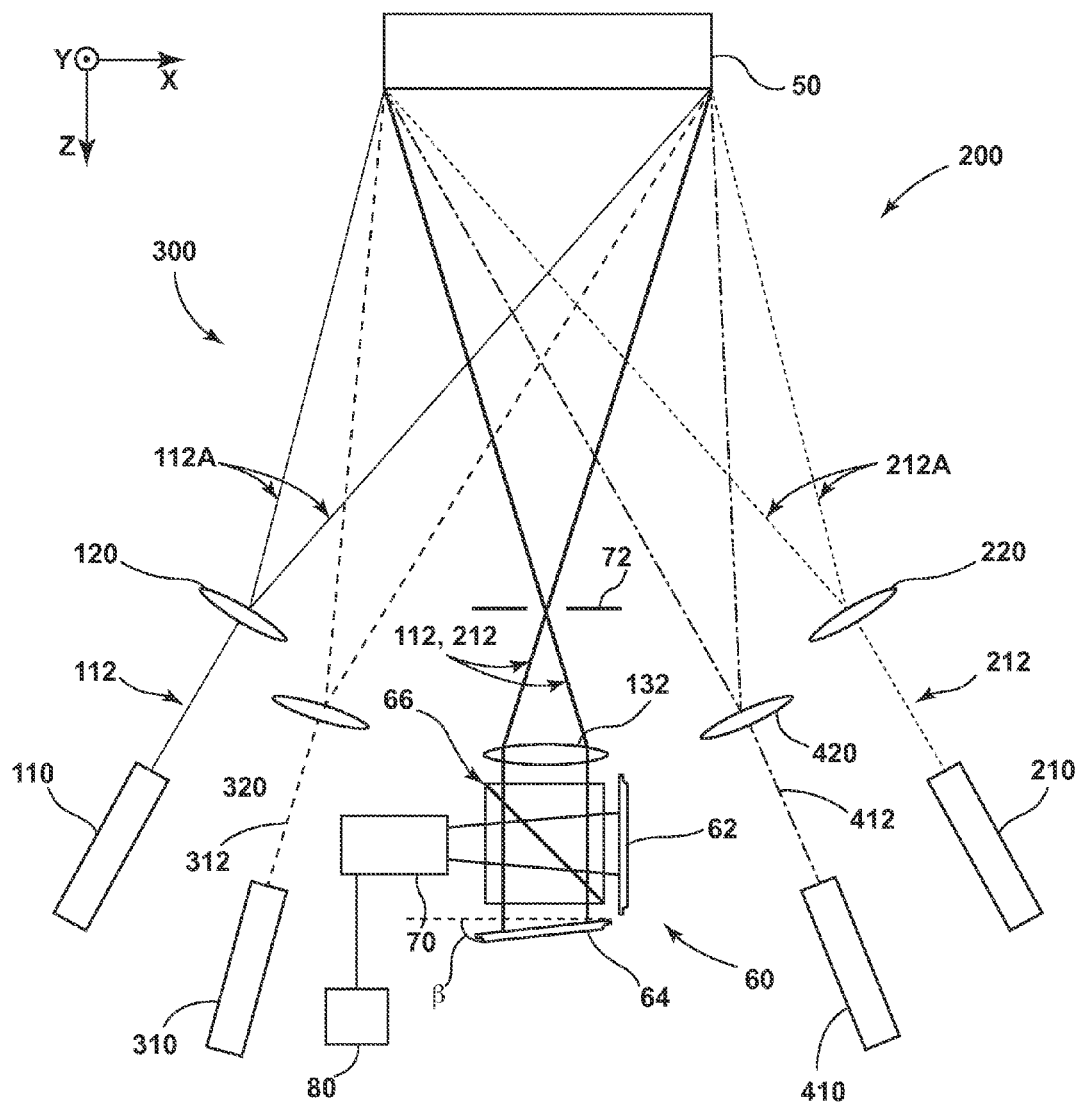
FIG. 11A is a schematic view of portions of an embodiment of a shearography system in accordance with teachings of the present disclosure.
Figure 11B:
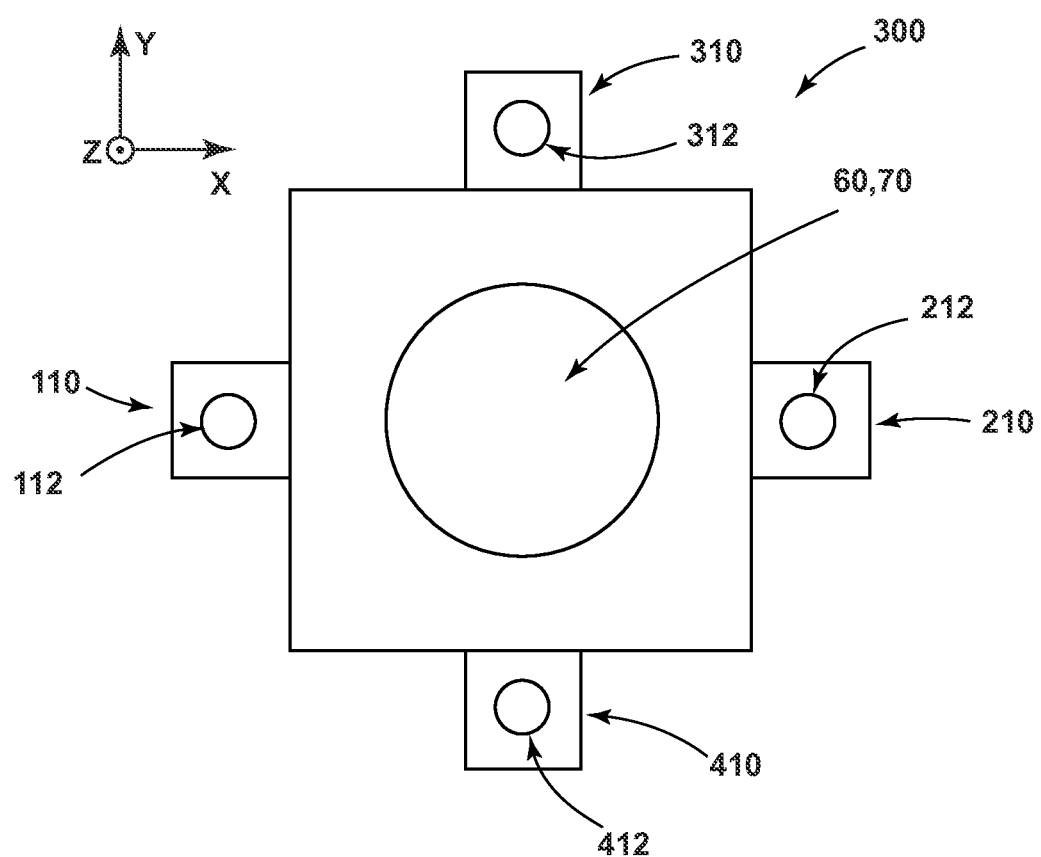
FIG. 11B is a schematic view of portions of an embodiment of a shearography system in accordance with teachings of the present disclosure.

In embodiments, as generally illustrated in FIGS. 11A and 11B, a shearography system (e.g., system 300) may include more than two light sources. For example, and without limitation, shearography may include a third light source 310 and/or a fourth light source 410. Third light source 310 may be configured to emit a third beam 312, which may include a third wavelength. Fourth light source 410 may be configured to emit a fourth beam 412, which may include a fourth wavelength. First, second, third, and fourth wavelengths may all differ from each other. A third beam expander 320 may be configured to expand third beam 312 and/or a fourth beam expander 420 may be configured to expand fourth beam 412.

In embodiments, including third light source 320 and/or fourth light source 420 may allow for illuminating test object 50 in more than one direction (e.g., in the x-direction and in the y-direction). Illuminating test object 50 in more than one direction may allow shearography system to simultaneously measure strain in a plurality of directions. For example and without limitation, all of a plurality of light sources (e.g., first light source 110, second light source 210, third light source 310, and fourth light source 410) may be configured to simultaneously illuminate an area of test object 50. First light source 110 and second light source 210 may provide illumination in the x-z plane (e.g., as generally illustrated in FIGS. 8A and 11A), and/or third light source 310 and/or fourth light source may provide illumination in the y-z plane (e.g., as generally illustrated in FIG. 11A). In embodiments, using at least three light sources with shearing in the x-direction may allow for measuring an x-direction component of in-plane normal strain in the x-direction, $$\frac{\partial u}{\partial x},$$

a y-direction component in-plane shear strain, $$\frac{\partial v}{\partial x},$$

and/or an x-direction component of out-of-plane shear strain, $$\frac{\partial w}{\partial x},$$

simultaneously and/or from a single image. In embodiments, using at least three light sources with shearing in the y-direction may allow for measuring an y-direction component of pure in-plane normal strain, $$\frac{\partial v}{\partial y},$$

a x-direction component pure in-plane shear strain, $$\frac{\partial u}{\partial y},$$

and/or an y-direction component of pure out-of-plane shear strain, $$\frac{\partial w}{\partial y},$$

simultaneously and/or from a single image.

In embodiments, first light source 110, second light source 210, third light source 310, and fourth light source 410 may simultaneously illuminate an area of test object 50 with first beam 112, second beam 212, third beam 312, and fourth beam 412, respectively. First beam 112 and second beam 212 may include wavelengths $\lambda_1$ and $\lambda_2$, respectively, and may be set in the X-Z plane. Third beam 312 and fourth beam 412 may include wavelengths $\lambda_3$ and $\lambda_4$, respectively, and may be set in the Y-Z plane. The illumination angle $\theta$ may be the same for each beam, and the following equations may represent the phase difference for each beam:

$$\Delta_1 = \frac{2\pi\Delta x}{\lambda_1}\left\{\frac{\partial u}{\partial x}\sin(+\theta) + \frac{\partial w}{\partial x}[1 + \cos(+\theta)]\right\}. \qquad \text{Eq. 43}$$

$$\Delta_2 = \frac{2\pi\Delta x}{\lambda_2}\left\{\frac{\partial u}{\partial x}\sin(-\theta) + \frac{\partial w}{\partial x}[1 + \cos(-\theta)]\right\}. \qquad \text{Eq. 44}$$

$$\Delta_3 = \frac{2\pi\Delta x}{\lambda_3}\left\{\frac{\partial v}{\partial x}\sin(+\theta) + \frac{\partial w}{\partial x}[1 + \cos(+\theta)]\right\}. \qquad \text{Eq. 45}$$

$$\Delta_4 = \frac{2\pi\Delta x}{\lambda_4}\left\{\frac{\partial v}{\partial x}\sin(-\theta) + \frac{\partial w}{\partial x}[1 + \cos(-\theta)]\right\}. \qquad \text{Eq. 46}$$

A resulting relationship for four beam illumination and shearing in the x direction may be:

$$\frac{\partial u}{\partial x} = \frac{\lambda_1\Delta_1 - \lambda_2\Delta_2}{4\pi\Delta x}. \qquad \text{Eq. 47}$$

$$\frac{\partial v}{\partial x} = \frac{\lambda_3\Delta_3 - \lambda_4\Delta_4}{4\pi\Delta x}. \qquad \text{Eq. 48}$$

A resulting value for $$\frac{\partial u}{\partial x}$$

and/or $$\frac{\partial v}{\partial x}$$

may be inserted into Equation 43 and/or Equation 44 to obtain $$\frac{\partial w}{\partial x}.$$

If the shearing direction is the y direction, a resulting relationship for a four light source illumination setup:

$$\frac{\partial u}{\partial y} = \frac{\lambda_1\Delta_1 - \lambda_2\Delta_2}{4\pi\Delta y}. \qquad \text{Eq. 49}$$

-continued $$\frac{\partial v}{\partial y} = \frac{\lambda_3 \Delta_3 - \lambda_4 \Delta_4}{4\pi \Delta y}.$$ Eq. 50

A resulting value for $$\frac{\partial u}{\partial y}$$

and/or $$\frac{\partial v}{\partial y}$$

may be inserted into Equation 45 and/or Equation 46 to obtain $$\frac{\partial w}{\partial y}.$$

For example, and without limitation, in a four light source illumination setup (e.g., as generally illustrated in FIGS. 11A and 11B), an x-direction shearing configuration may permit measuring three individual strain components:

$$\frac{\partial u}{\partial x}, \frac{\partial v}{\partial x},$$

and $$\frac{\partial w}{\partial x}$$

in one measurement (e.g., not just a total strain measurement). In embodiments, a y-direction shearing configuration may permit measuring three individual strain components:

$$\frac{\partial u}{\partial y}, \frac{\partial v}{\partial y},$$

and $$\frac{\partial w}{\partial y}$$

in one measurement.

In embodiments, camera 70 may be configured to obtain intensity information corresponding to each of the plurality of light sources illuminating test object 50. The intensity information may include reference intensity information that may be obtained while test object 50 is in a reference state and may include testing intensity information that may be obtained while test object is in a testing state. The reference intensity information may include a plurality of interferograms that may each correspond to a particular light source. For example, and without limitation, a plurality of reference interferograms may include a first interferogram that may correspond to first light source, a second interferogram that may correspond to second light source 210, a third interferogram that may correspond to third light source, 310, and/or a fourth interferogram that may correspond to fourth light source. Camera 70 may be configured to capture some or all of the first interferogram, the second interferogram, the third interferogram, and/or the fourth interferogram in a single reference image.

In embodiments, testing intensity information may include a plurality of interferograms that may each correspond to a particular light source. A plurality of testing interferograms may include a fifth interferogram that may correspond to first light source, a sixth interferogram that may correspond to second light source 210, a seventh interferogram that may correspond to third light source, 310, and/or an eighth interferogram that may correspond to fourth light source. Camera 70 may be configured to capture some or all of the fifth interferogram, the sixth interferogram, the seventh interferogram, and/or the eighth interferogram in a single testing image.

In embodiments, a shearography system may be configured to determine a strain measurement from only a single reference image and a single testing image.

In embodiments, an interferogram may include one or more image components. Image components may correspond to a particular light source, the wavelength of a light produced by the particular light source, and/or the shearing angle. For example, and without limitation, a first interferogram may correspond to first light source 110 (e.g., result from first beam 112 reflecting off of test object 50) and/or may include two image components that have been sheared by shearing angle β. As described above, an amount of shearing between the two image components may correspond to the wavelength of first beam 112 and shearing angle β. In embodiments, image components may be identical.

In embodiments, a reference image may be acquired before testing begins. One or more testing images may be captured and processed generally according to the process shown and/or described in connection with FIG. 10. In embodiments, a shearography system may be configured to acquire a series of testing images and process each test image as it is acquired, such as, for example, in real-time or near real-time. In embodiments, a shearography system may, additionally or alternatively, be configured to acquire a series of testing images and process the images at a later time, such as, for example, after testing of the test object is complete.

In embodiments, a reference image may be updated with the most recent testing image and then compared to a new test image. For example, and without limitation, a reference image may be obtained of an unloaded test object and a first testing image may be obtained of the test object under a first load. The reference image may then be compared to the first testing image, which may permit a determination of strain. Then, the reference image may be updated with the first testing image and compared with a second testing image that may be obtained of the test object under a second load, which may permit a second determination of strain.

It should be understood that embodiments (e.g., shearography system 100 and/or shearography system 200) do not require a temporal phase shift to determine strain. It should also be understood that switching between light sources located in difference places may not be required. For example, different wavelengths of first, second, third, and/or fourth light sources 110, 210, 310, 410 may allow for all light sources to be simultaneously illuminated and/or directed toward a test object 50, which may allow for camera 70 to acquire a single image containing multiple distinguishable speckle inteferograms. Thus, during testing, embodiments of a shearography system may be configured to process a single testing image acquired, without requiring a shutter operation, and compare it to a single reference image to determine strain (e.g., shearography system 100 and/or shearography system 200 may use as few as two total images, which may each contain a plurality of speckle interferograms, to determine strain).

Figure 12:
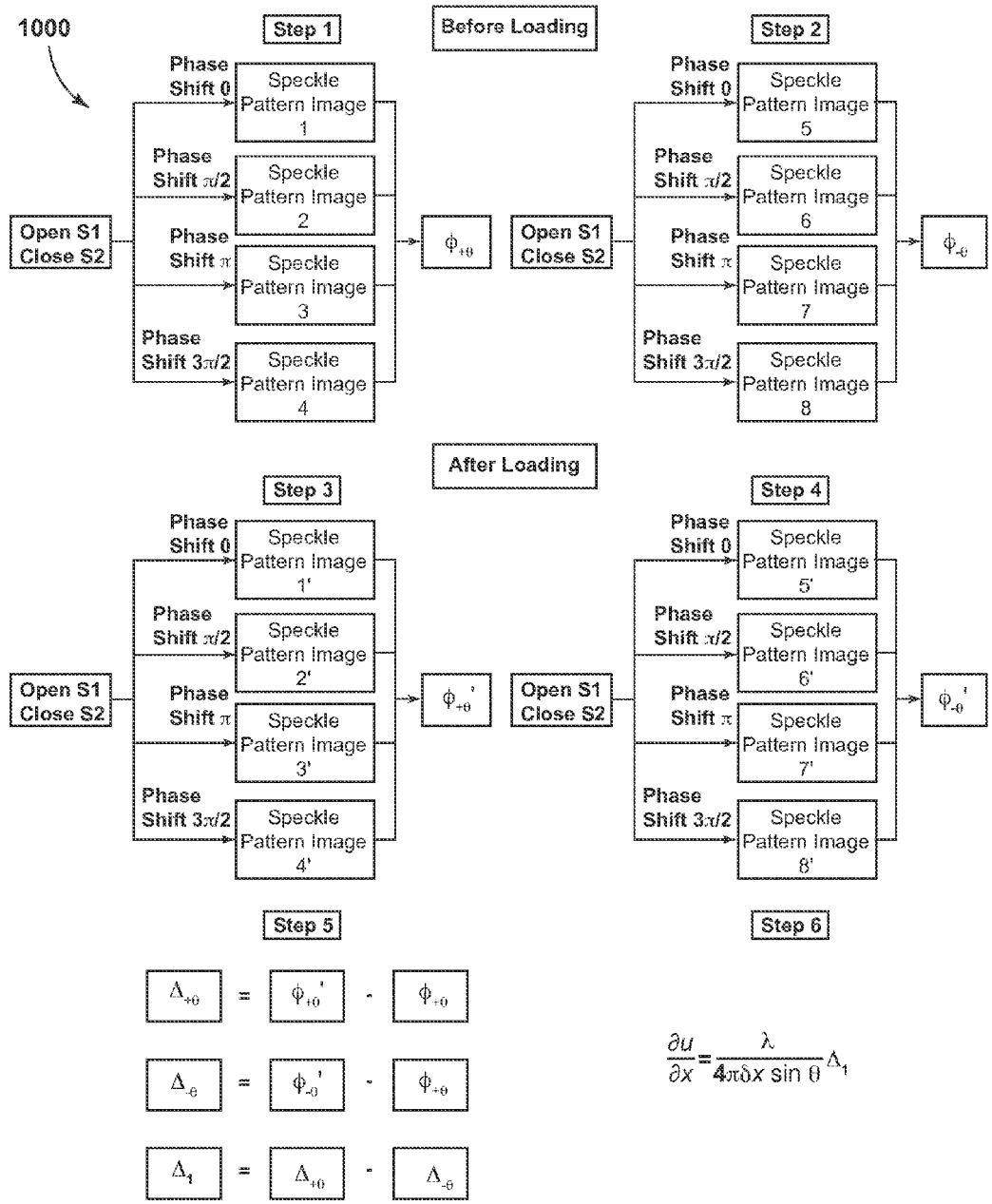
FIG. 12 is a block diagram of a method determining strain according to a conventional system.

In contrast, in conventional shearography systems 1000, as generally illustrated in FIG. 12, measuring in-plane strain may involve four shutter operations (e.g., one shutter operation each of step 1, step 2, step 3, and step 4), 16 phase-shift steps, and 16 speckle pattern images. Such a complicated process may involve a relatively significant amount of time during which strain on a test object should remain constant. In embodiments of the present disclosure, camera 70 may continuously obtain intensity information (e.g., without discrete shutter operations) and may be configured to communicate that intensity information to processor 80. Thus, conventional shearography systems may be limited to static measurements (e.g., because the test object must remain still/have the same loading during the relatively lengthy image acquisition and shutter operations), as opposed to embodiments of the present disclosure, which may be capable of dynamic and/or partially dynamic strain measurements.

Embodiments of the present disclosure may include one or more advantages relative to conventional systems, such as the system 1000 generally represented in FIG. 12. An advantage of embodiments of the present disclosure (e.g., of shearography system 100 and/or shearography system 200) may include a greater measuring speed, which may result from using fewer images, using fewer and/or zero shutter operations, and/or from making fewer adjustments to system. For example, in embodiments, all components of shearography system 100 and/or shearography system 200, other than test object 50, may be configured to remain substantially stationary during measurement/use. Additionally or alternatively, embodiments of a shearography system 100, 200 may be configured such that few or none of its components are adjusted during testing. For example, and without limitation, light sources (e.g., light sources 110, 210, 310, 410), optical shearing device 60, which may include mirror 62 and/or mirror 64, may not be adjusted (e.g., may remain in substantially the same position relative to each other and/or testing object 50) during use. In embodiments, a sampling rate of measurement may be extremely close to an acquisition rate of camera (e.g., because shifts and shutter operations may not be required), which may enable measurement of dynamic loading with a sufficiently high-speed camera.

Another advantage of embodiments of a shearography system 100, 200 may include a simpler structure with better resulting image quality relative to conventional systems, such as conventional Mach-Zehnder interferometer-based shearography. For example, embodiments of shearography system 100 may include fewer beam splitters (e.g., one for each light source), fewer mirrors (e.g., two), and/or a shorter image distance, which may permit higher quality phase maps.

Another advantage of embodiments of a shearography system according to the present disclosure (e.g., shearography system 100 and/or shearography system 200) may include an adjustable field of view. For example, and without limitation, in embodiments including a 4f system, a field of view may be adjusted not only by an image lens 132, but may also be adjusted via lens 134 and/or lens 136.

Another advantage of embodiments of a shearography system according to the present disclosure may include the ability to measure pure out-of-plane strain components $$\left(e.g., \frac{\partial w}{\partial x}, \frac{\partial w}{\partial y}\right).$$

In conventional systems, measurement of out-of-plane strain components are not pure because such measurements inevitably include at least some elements of other strain components (e.g., in-plane strain components).

It should be understood that, in embodiments, at least some of the steps of determining a strain measurement could be completed in real-time, near real-time, or offline. For example, a series of images of a dynamic test object could be collected over a period of time and later analyzed to determine strain. Additionally or alternatively, the efficiency of analyzing a single image before loading and a single image after loading may allow for faster processing times that may approach real-time or effectively be real-time.

The foregoing descriptions of specific embodiments of the present invention have been presented for purposes of illustration and description. They are not intended to be exhaustive or to limit the invention to the precise forms disclosed, and various modifications and variations are possible in light of the above teaching. It should be understood that references to a single element are also intended to include embodiments that may include more than one of that element or zero of that element. For example, references to a light source are intended to include embodiments with one light source or more than light source. Also, references to a light source are not limited to a particular type of light source or laser and are intended to include any type of light source or other component with similar functionality.

The embodiments and examples were chosen and described to explain the principles of the invention and a practical application, to thereby enable others skilled in the art to utilize the invention and various embodiments with various modifications as are suited to the particular use contemplated. It is intended that the scope of the invention be defined by the claims and their equivalents.

What is claimed is:
1. A shearography system comprising:
   a plurality of light sources each configured to produce a beam of light to illuminate a test area, each of the beams of light having a different wavelength;
   a camera configured to obtain intensity information corresponding to reflections of the plurality of light sources off of the test area in a single testing image and a single reference image;
   an optical shearing device disposed in an optical path between the plurality of light sources and the camera, the optical shearing device including a plurality of mirrors and configured to provide a shearing angle;
   a processor configured to determine a strain measurement corresponding to the test area in two directions entirely from the single reference image and the single testing image via spatial phase-shifting; and
   wherein the plurality of light sources comprises a first light source configured to produce a first light having a first wavelength, a second light source configured to produce a second light having a second wavelength, and a third light source configured to produce a third light having a third wavelength;

wherein the strain measurement includes an in-plane strain measurement and an out-of-plane strain measurement;

the camera is configured to obtain the testing image while the first light source, the second light source, and the third light source are simultaneously illuminating the test area and spatially overlapping at the test area;

the single testing image includes a first interferogram corresponding to the first light source, a second interferogram corresponding to the second light source, and a third interferogram corresponding to the third light source;

the first interferogram, the second interferogram, and the third interferogram overlap spatially in the camera; and wherein the optical shearing device is configured as a Michelson interferometer.

2. The system of claim 1, comprising a fourth light source configured to provide a fourth light having a fourth wavelength; wherein the camera is configured to:

obtain the reference image while the first light source, the second light source, the third light source, and the fourth light source are simultaneously illuminating the test area while the test area is in a reference state, wherein the single reference image includes a fourth interferogram corresponding to the fourth light source; and obtain the testing image while the first light source, the second light source, the third light source, and the fourth light source are simultaneously illuminating the test area while the test area is in a testing state, wherein the single testing image includes a fifth interferogram corresponding to the first light source, a sixth interferogram corresponding to the second light source, a seventh interferogram corresponding to the third light source, and an eighth interferogram corresponding to the fourth light source.

3. The system of claim 2, wherein each of the first interferogram, the second interferogram, the third interferogram, the fourth interferogram, the fifth interferogram, the sixth interferogram, the seventh interferogram, and the eighth interferogram include a pair of sheared image components sheared by the shearing angle.

4. The system of claim 1, wherein the plurality of light sources, the camera, and the plurality of mirrors are configured to remain substantially stationary relative to each other and relative to the test area during strain measurements.

5. The system of claim 1, wherein the processor is configured to apply a Fourier transform to the reference image to generate a reference spectrum and to apply a windowed inverse Fourier transform to the reference spectrum to generate a phase map corresponding to the reference image; and a window of the windowed inverse Fourier transform corresponds to the first wavelength and the shearing angle.

6. The system of claim 5, wherein the processor is configured to apply a Fourier transform to the testing image to generate a testing spectrum and to apply a windowed inverse Fourier transform to the testing spectrum to generate a phase map corresponding to the testing image; and a window of the windowed inverse Fourier transform for the testing spectrum corresponds to the second wavelength and the shearing angle.

7. The system of claim 1, wherein the first light source and the second light source provide illumination in a first plane and the third light source and a fourth light source provide illumination in a second plane perpendicular to the first plane.

8. A method of determining strain, the method comprising:

illuminating, via a plurality of light sources simultaneously, a test area of a test object;

capturing, via a single camera, a single reference image;

capturing, via the camera, a single testing image; and determining a strain measurement solely from the single reference image and the single testing image via spatial phase-shifting;

wherein each of the light sources of the plurality of light sources is configured to produce a beam of light; the beam of light produced by each light source has a different wavelength than the beam of light produced by each other light source; the beam of light produced by each light source spatially overlaps with the beam of light produced by each other light source at the test area;

the strain measurement includes an in-plane strain measurement and an out-of-plane strain measurement;

capturing the single reference image includes capturing a plurality of spatially overlapping interferograms, each interferogram corresponding to a respective light source of the plurality of light sources; and the beam of light produced by each light source propagates from the test area to a Michelson interferometer and then to the single camera.

9. The method of claim 8, wherein the plurality of light sources includes four light sources configured to simultaneously illuminate the test area.

10. The method of claim 9, wherein the reference image includes a first plurality of interferograms, the testing image includes a second plurality of interferograms; and the first plurality of interferograms and the second plurality of interferograms are captured via the camera while the four light sources are simultaneously illuminating the test area.

11. A method of determining strain, the method comprising:

illuminating, via a plurality of light sources simultaneously, a test area of a test object such that light from the plurality of light sources spatially overlaps at the test area;

capturing, via a camera, a single reference image of the test object;

capturing, via the camera, a single testing image of the test object; and determining a strain measurement solely from the single reference image and the single testing image via spatial phase-shifting;

wherein determining the strain measurement includes applying a Fourier transform to the reference image to generate a reference spectrum, and applying a windowed inverse Fourier transform to the reference spectrum to generate a phase map corresponding to the reference image;

the strain measurement includes an in-plane strain measurement and an out-of-plane strain measurement; capturing the single reference image includes capturing a plurality of spatially overlapping interferograms corresponding to the plurality of light sources; light from each light source of the plurality of light sources has a different wavelength; and a Michelson interferometer is disposed in an optical path of light from the plurality of light sources between the test area and the camera.

12. The method of claim 11, wherein determining the strain measurement includes:
applying a Fourier transform to the testing image to generate a testing spectrum; and
applying a windowed inverse Fourier transform to the testing spectrum to generate a phase map corresponding to the testing image.

13. The method of claim 11, wherein a window of the windowed inverse Fourier transform corresponds to a shearing angle of the Michelson interferometer.

14. The method of claim 13, wherein the reference spectrum includes a first frequency component and a second frequency component; the first frequency component corresponds to the shearing angle and a first wavelength of a first light source of the plurality of light sources; and the second frequency component corresponds to the shearing angle and a second wavelength of a second light source of the plurality of light sources.

* * * * *